(12) United States Patent
Daniel et al.

(10) Patent No.: US 11,744,918 B2
(45) Date of Patent: Sep. 5, 2023

(54) TRANSLUCENT, DEHYDRATED PLACENTAL TISSUE AND METHODS OF PRODUCING AND USING THE SAME

(71) Applicant: StimLabs LLC, Roswell, GA (US)

(72) Inventors: John Daniel, Milton, GA (US); Sarah Griffiths, Sandy Springs, GA (US); Annelise Mowry Roy, Cumming, GA (US)

(73) Assignee: StimLabs LLC, Roswell, GA (US)

( * ) Notice: Subject to any disclaimer, the term of this patent is extended or adjusted under 35 U.S.C. 154(b) by 0 days.

(21) Appl. No.: 17/486,638

(22) Filed: Sep. 27, 2021

(65) Prior Publication Data

US 2022/0080080 A1 Mar. 17, 2022

Related U.S. Application Data

(63) Continuation of application No. 16/225,733, filed on Dec. 19, 2018, now Pat. No. 11,154,641.

(60) Provisional application No. 62/609,771, filed on Dec. 22, 2017.

(51) Int. Cl.
| | |
|---|---|
| A61L 27/36 | (2006.01) |
| A61P 17/02 | (2006.01) |
| A61L 27/54 | (2006.01) |
| A61K 35/50 | (2015.01) |
| A61L 27/50 | (2006.01) |

(52) U.S. Cl.
CPC .......... *A61L 27/3604* (2013.01); *A61K 35/50* (2013.01); *A61L 27/3691* (2013.01); *A61L 27/50* (2013.01); *A61L 27/54* (2013.01); *A61P 17/02* (2018.01); *A61L 2430/40* (2013.01)

(58) Field of Classification Search
CPC ..... A61K 35/50; A61K 35/51; A61L 2430/40; A61L 27/3604; A61L 27/3691; A61L 27/54; A61L 27/50; A61P 17/02
See application file for complete search history.

(56) References Cited

U.S. PATENT DOCUMENTS

| | | |
|---|---|---|
| 8,231,908 B2 | 7/2012 | Kinoshita et al. |
| 8,323,701 B2 | 12/2012 | Daniel et al. |
| 8,409,626 B2 | 4/2013 | Daniel et al. |
| 8,414,929 B2 | 4/2013 | Nikaido et al. |
| 8,685,732 B2 | 4/2014 | Perez et al. |
| 8,709,494 B2 | 4/2014 | Daniel |
| 8,932,641 B2 | 1/2015 | Nikaido et al. |
| 9,084,767 B2 | 7/2015 | Daniel et al. |
| 9,186,382 B2 | 11/2015 | Daniel et al. |
| 9,486,316 B2 | 11/2016 | Horton et al. |
| 9,539,104 B2 | 1/2017 | Horton et al. |
| 9,687,588 B2 | 6/2017 | Daniel et al. |
| 11,116,871 B2 | 9/2021 | Daniel et al. |
| 11,154,641 B2 | 10/2021 | Daniel et al. |
| 11,413,372 B2 * | 8/2022 | Daniel ............... A61L 27/3604 |
| 2005/0107876 A1 | 5/2005 | Kim et al. |
| 2011/0189301 A1 | 8/2011 | Yang et al. |
| 2012/0083900 A1 | 4/2012 | Samaniego et al. |
| 2013/0136773 A1 | 5/2013 | Horton et al. |
| 2013/0218274 A1 | 8/2013 | Spencer et al. |
| 2014/0050788 A1 | 2/2014 | Daniel et al. |
| 2014/0186461 A1 | 7/2014 | Broussard |
| 2014/0271728 A1 | 9/2014 | Koob et al. |
| 2015/0216910 A1 | 8/2015 | Horton et al. |
| 2016/0136328 A1 | 5/2016 | LeVaughn et al. |
| 2017/0086961 A1 | 3/2017 | Ganey |
| 2017/0246348 A1 | 8/2017 | Daniel et al. |

FOREIGN PATENT DOCUMENTS

| | | |
|---|---|---|
| EP | 3349812 B1 | 1/2021 |
| WO | 9310722 A2 | 6/1993 |
| WO | 2004028584 A1 | 4/2004 |
| WO | 2006026325 A2 | 3/2006 |
| WO | 2007114809 A1 | 10/2007 |
| WO | 2009033160 A1 | 3/2009 |
| WO | 2012088396 A2 | 6/2012 |
| WO | 2012112410 A2 | 8/2012 |
| WO | 2013049052 A2 | 4/2013 |
| WO | 2013082412 A1 | 6/2013 |
| WO | 2016081386 A1 | 5/2016 |
| WO | 2017049210 A1 | 3/2017 |

(Continued)

OTHER PUBLICATIONS

Koob, T., et al., "Angiogenic properties of dehydrated human amnion/chorion allografts: therapeutic potential for soft tissue repair and regeneration," Vasc Cell 2014, 6:10, doi: 10.1186/2045-824X-6-10, 10 pages.

Koob, T., et al., "Biological properties of dehydrated human amnion/chorion composite graft: implications for chronic wound healing," Int Wound J, 2013, 10(5):493-500.

Koob, T., et al., "Cytokines in single layer amnion allografts compared to multilayer amnion/chorion allografts for wound healing," J Biomed Mater Res B Appl Biomater, 2015, 103B:1133-1140.

Koob, T., et al.,"Properties of dehydrated human amnion/chorion composite grafts: Implications for wound repair and soft tissue regeneration," J Biomed Mater Res, Part B, 2014:102(6):1353-1362, doi:10.1002/jbm.b.33141, 10 pages.

(Continued)

*Primary Examiner* — Aaron J Kosar
(74) *Attorney, Agent, or Firm* — McNeill Baur PLLC

(57) ABSTRACT

Compositions comprising translucent, dehydrated placental tissue and methods of preparing and using those tissues are provided. Repeated dehydration techniques may produce translucent, dehydrated placental tissues, including translucent, dehydrated placental membrane and umbilical cord, with improved visualization and/or handling characteristics. The present invention also includes methods of healing a wound of the skin, eye, nerve, tendon, muscle, dental region, or dura, including burns, comprising applying the translucent, dehydrated placental tissues of the invention to the wound.

24 Claims, 8 Drawing Sheets

(56) References Cited

FOREIGN PATENT DOCUMENTS

| | | |
|---|---|---|
| WO | 2017049215 A1 | 3/2017 |
| WO | 2017112934 A1 | 6/2017 |

OTHER PUBLICATIONS

Kruse, F., et al., "Cryopreserved human amniotic membrane for ocular surface reconstruction," Graefe's Arch Clin Exp Ophthalmol, 2000, 238(1):68-75.
Laurent, T., et al., "Hyaluronan in inflammatory joint disease," Acta Orthop Scand, 1995, 66:116-120.
Libera, R., et al., "Assessment of the use of cryopreserved x freeze-dried amniotic membrane (AM) for reconstruction of ocular surface in rabbit model," Arq Bras Oftalmol, 2008, 71(5):669-73.
Malak, T.M., et al., "Confocal Immunofluorescence Localization of Collagen Types I, III, IV, V and VI and their Ultrastructural Organization in Term Human Fetal Membranes," Placenta, 1993, 14(4):385-406.
Malkowski, A., et al., "FGF binding by extracellular matrix components of Wharton's jelly," Acta Biochim Pol., 2007, 54(2):357-63 and references, 2 pages.
Mamede, A.C., et al., "Amniotic membrane: from structure and functions to clinical applications," Cell Tissue Res, 2012, 349(2):447-58.
Meinert, M., et al., "Proteoglycans and hyaluronan in human fetal membranes," Am J Obstet Gynecol, 2001, 184(4):679-85.
MiMedx Purion Process, accessed from https://mimedx.com/purion-process/ on Sep. 9, 2019, 3 printed pages.
Mohammadi, A., et al., Chapter 18, "How Does Human Amniotic Membrane Help Major Burn Patients Who Need Skin Grafting: New Experiences," Skin Grafts—Indications, Applications and Current Research, Ed. M. Spear, In Tech, 2011, pp. 265-276, 13 pages.
Nakamura, T., et al., "Novel clinical application of sterilized, freeze-dried amniotic, membrane to treat patients with pterygium," Acta Ophthalmol Scand, 2006, 84(3):401-5.
Nakamura, T., et al., "Sterilized, Freeze-Dried Amniotic Membrane: A Useful Substrate for Ocular Surface Reconstruction," IOVS, 2004, 45(1):93-99.
Necas, J., et al., "Hyaluronic acid (hyaluronan): a review," Veterinarni Medicina, 2008 53(8):397-411.
Nichols, F. and Overly A., "Novel Approach for Enterocutaneous Fistula Treatment with the Use of Viable Cryopreserved Placental Membrane," Case Rep Surg. 2016, Article ID 8797691, 4 pages.
Niknejad, H., et al., "Properties of the Amniotic Membrane for Potential Use in Tissue Engineering," Eur Cell Mater, 2008, 15:88-99.
Nogi, M., et al., "Optically Transparent Nanofiber Paper," Adv Mater, 2009, 21:1595-98.
NuShield™ Extraordinary Properties, Everyday Utility, NuShield-202 Brochure, 2 pages (2015).
Palka, J., et al., "An accumulation of IGF-1 and IGF-binding proteins in human umbilical cord," Mol Cell Biochem, 2000, 206(1-2):133-9.
Park, C., et al., "Immunosuppressive Property of Dried Human Amniotic Membrane," Ophthalmic Res, 2009, 41(2):112-3, Epub 2008.
Parolini, O., et al., Chapter 1, "Human Term Placenta as a Therapeutic Agent: From the First Clinical Applications to Future Perspectives," In Human Placenta: Structure and Development, Circulation and Functions. E. Berven & A. Freberg (Eds.), Nova Science Publishers, Inc., 2010, pp. 1-49.
Raio, L., et al., "Hyaluronan content of Wharton's jelly in healthy and Down syndrome fetuses," Matrix Biol. 2005, 24(2):166-74.
Reddy, U. et al., "In vitro sealing of punctured fetal membranes: Potential treatment for midtrimester premature rupture of membranes," Am J Obstet Gynecol, 2001, 185(5):1090-93.
Revita, The First Intact Amniotic Membrane Allograft, StimLabs, accessed from https://www.stimlabs.com/revita on Aug. 7, 2020 (7 pages).
Revita® Pamphlet, StimLabs, MKTG19-007Rev01 (2019) (3 pages).
Revita® Wound Application Guide, Dehydrated Human Placental Membrane Allograft, StimLabs, MKTG 18-002 Rev 01 (2018) (2 pages).
Revita®, The Optimal Barrier Membrane, StimLabs, MKTG18-027 Rev 02 (2018) (2 pages).
Robson, M., et al., "Amniotic Membranes as a Temporary Wound Dressing," Surg Gynecol Obstet, 1973, 136(6):904-6.
Robson, M., et al., "Quantitative Comparison of Biological Dressings," J Surg Res. 1973, 14(5):431-4.
Rodriguez-Ares, M., et al., "Effects of lyophilization on human amniotic membrane," Acta Ophthalmol, 2009, 87(4):396-403.
Romanowicz, L. & Galewska, Z., "Extracellular Matrix Remodeling of the Umbilical Cord in Pre-eclampsia as a Risk Factor for Fetal Hypertension," J Pregnancy, 2011, doi: 10.1155/2011/542695, Epub Dec. 29, 2010, pp. 1-9.
Rousselle, P., et al., "Laminin 5 Binds the NC-1 Domain of Type VII Collagen," J Cell Biol, 1997, 138(3)719-28.
Roy et al., "Intermediate layer contribution in placental membrane allografts", J. Tissue Eng Regen Med., pp. 1-10 (2020), with supplemental figure 1.
Ryynänen, J., et al., "Type VII Collagen Gene Expression in Human Umbilical Tissue and Cells," Lab Invest, 1993, 69(3):300-4.
Sabella, N., "Use of the Fetal Membranes in Skin Grafting," Medical Record, A Weekly Journal of Medicine and Surgery, 1913, 83:478-80.
Smith, J. & Ockleford, C.D., "Laser Scanning Confocal Examination and Comparison of Nidogen (Entactin) with Laminin in Term Human Amniochorion," Placenta, 1994, 15(1):95-106.
Sobolewski, K., "Wharton's Jelly as a Reservoir of Peptide Growth Factors," Placenta, 2005, 26(10):747-52, Epub Dec. 15, 2004.
Sobolewski, K., et al., "Binding of the basic fibroblast growth factor (bFGF) by soluble components of human umbilical cord," Acta Biochim Pol., 2002 49(4):999-1004.
Sobolewski, K., et al., "Collagen and Glycosaminoglycans of Wharton's Jelly," Biol Neonate, 1997, 71(1):11-21.
Stern, M., "The Grafting of Preserved Amniotic Membrane to Burned and Ulcerated Surfaces, Substituting Skin Grafts," JAMA, 1913, 60(13):973-4.
StimLabs Announces Enrollment of First Patient in Evaluating Efficacy of Full Thickness Placental Allograft, Revita®, in Lumbar Microdisectomy Outcomes, Jun. 19, 2018 (accessed from https://www.pmewswire.com/news-releases/stimlabs-announces-enrollment-of-first-patient-in-evaluating-efficacy-of-full-thickness-placental-allograft-revita-in-lumbar-microdiscectomy-outcomes-300668450.html?tc=eml_cleartime on Jan. 26, 2021), 3 pages.
Tan, E., et al., "Structural and Biological Comparison of Cryopreserved and Fresh Amniotic Membrane Tissues," J Biomater Tissue Eng, 2014, 4(5):379-388.
Tseng, S., et al., "How Does Amniotic Membrane Work?" The Ocular Surface, 2004, 2(3):177-87.
"Efficacy of a Full-Thickness Placental Allograft in Lumbar Microdiscectomy", ClincialTrials.gov Identifier:NCT03536013 (May 24, 2018), (accessed from https://www.clinicaltrials.gov/ct2/show/NCT03536013?term=stimlabs&draw=2&rank=3 on Jan. 26, 2021), 6 pages.
"Efficacy of Human Placental Graft in Diabetic Foot Ulcers", ClinicalTrials.gov Identifier: NCT03708029 (Oct. 16, 2018) (accessed from https://www.clinicaltrials.gov/ct2/show/results/NCT03708029?term=stimlabs&draw=2&rank=1 on Jan. 26, 2021), 6 pages.
"LifeNet Health is reimagining wound healing with Matrion™, the first fully intact and complete placental membrane" (Nov. 4, 2020) (downloaded from https://www.prnewswire.com/news-releases/lifenet-health-is-reimagining-wound-healing-with-matrion-the-first-fully-intact-and-complete-placental-membrane-301166304.html on Feb. 19, 2021) (3 pages).
Abshier, S., "A closer look at the potential of placental membrane grafts for chronic diabetic foot ulceration," Podiatry Today, 2015, 28(11):20-26, 12 printed pages.
Arno, A., et al., "Stem Cell Therapy: A New Treatment for Burns?" Pharmaceuticals, 2011, 4(10):1355-80.
Arpino, A., et al., "The role of TIMPs in regulation of extracellular matrix proteolysis," Matrix Biol, 2015, 44-66:247-54.

(56) References Cited

OTHER PUBLICATIONS

Baergen, R., Chapter 6, "Histology of the Chorionic Villi, Fetal Membranes, and Umbilical Cord," Manual of Benirschke and Kaufmann's Pathology of the Human Placenta, Springer Science+Business Media, Inc., 2005, pp. 80-95.
Baergen, R., et al., Chapter 7, "Overview and Microscopic Survey of the Placenta," Manual of Pathology of the Human Placenta, Springer + Business Media, LLC, 2011, pp. 85-108.
Bańkowski, E., et al., "Collagen and glycosaminoglycans of Wharton's Jelly and their alterations in EPH-gestosis," Eur J Obstet Gynecol Reprod Biol. 1996, 66(2):109-17.
Benirschke K., et al., Chapter 11, "Anatomy and Pathology of the Placental Membranes," Pathology of the Human Placenta, Springer-Verlag Berlin Heidelberg, 2012, pp. 249-307.
Bhushan, K., et al., "Amniotic membrane & its structure, features and uses in dentistry—a brief review," Int J Adv Res, 2015, 3(11):354-60.
Blanco, M., et al., "Histopathology and histomorphometry of umbilical cord blood vessels. Findings in normal and high risk pregnancies," Artery Research, 2011, 5(2):50-7, doi:10.1016/j.artres.2011.02.001, article in-press version, pp. 1-8.
Bourne, G., "The Foetal Membranes, A Review of the Anatomy of Normal Amnion and Chorion and Some Aspects of Their Function," Postgrad. Med. J., 1962, 38:193-201.
Bryant-Greenwood, G., "The Extracellular Matrix of the Human Fetal Membranes: Structure and Function," Placenta, 1998, 19(1):1-11.
Bujang-Safawi, E., et al., "Dried irradiated human amniotic membrane as a biological dressing for facial burns—A 7-year case series," Burns, 2010, 36(6):876-82.
Can, A. & Karahuseyinoglu, S., "Concise Review: Human Umbilical Cord Stroma with Regard to the Source of Fetus-Derived Stem Cells," Stem Cells, 2007, 25(11):2886-95.
Chan, R., et al., "The Human Umbilical Vein with Wharton's Jelly as an Allogeneic, Acellular Construct for Vocal Fold Restoration," Tissue Eng Part A, 2009, 15(11):3537-46.
Clarification on Revita, StimLabs, (accessed from https://static1.squarespace.com/static/5798cb8c1b631b57d81149b3/t/5d6eb56ae3fdc70001735701/1567536491665/Clarification+on+Revita.pdf on Jan. 26, 2021), 8 pages.
Corrao, S., et al., "Umbilical cord revisited: from Wharton's jelly myofibroblasts to mesenchymal stem cells," Histol Histopathol, 2013, 28(10):1235-44.
Davis, J.S., "Skin Transplantation. With a Review of 550 Cases at the Johns Hopkins Hospital," The Johns Hopkins Hospital Reports, vol. XV, pp. 308-396, 91 pages, 1910.
De Rötth, A., "Plastic Repair of Conjunctival Defects with Fetal Membranes," Arch Ophthalmol, 1940, 23(3):522-525.
Dino, B., et al., "Human Amnion: The Establishment of an Amnion Bank and its Practical Applications in Surgery," J Philipp Med Assoc, 1966, 42(7):357-66.
Douglas, B., "Homografts of Fetal Membranes as a Covering for Large Wounds—Especially Those From Burns," J Tn State Med Assoc, 1952, 45(6):230-5.
Dua, H., et al., "Amniotic membrane transplantation," Br J Ophthalmol, 1999, 83:748-752.
Fetterolf D., et al., "Scientific and Clinical Support for the Use of Dehydrated Amniotic Membrane in Wound Management," Wounds, 2012, 24(10):299-307.
File History of U.S. Appl. No. 15/760,753, "Compositions Derived from Placenta and Methods of Producing the Same" in the name of John Daniel et al., filed Mar. 16, 2018.
File History of U.S. Appl. No. 15/760,757, "Compositions Derived from Placenta and Methods of Producing the Same" in the name of John Daniel et al., filed Mar. 16, 2018.
Franc, S., et al., "Microfibrillar Composition of Umbilical Cord Matrix: Characterization of Fibrillin, Collagen VI and Intact Collagen V," Placenta, 1998, 19(1):95-104.
Full Thickness Native Placental Membrane, StimLabs, MKTG18-019 Rev 01 (1 page).
Galewska, Z. & Romanowicz, L., "The Membrane-Type Matrix Metalloproteinases (MT1-MMP and MT2-MMP) of the Umbilical Cord," Archives of Perinatal Medicine, 2011, 17(3):158-63.
Ganatra, M.A., "Amniotic Membrane in Surgery," J Pak Med Assoc, 2003, 53(1), 7 pages.
Ganatra, M.A., "Method of Obtaining and Preparation of Fresh Human Amniotic Membrane for Clinical Use," J Pak Med Assoc, 1996, 46(6):126-8, 5 pages.
Gibbons G.W., "Grafix®, a Cryopreserved Placental Membrane, for the Treatment of Chronic/Stalled Wounds," Adv Wound Care, 2015, 4(9):534-44.
Goa, K.L. & Benfield, P., "Hyaluronic Acid: A Review of its Pharmacology and Use as a Surgical Aid in Ophthalmology, and its Therapeutic Potential in Joint Disease and Wound Healing," Drugs, 1994, 47(3):536-66.
Gonzalez-Gutierrez, J., et al., "Development of highly-transparent protein/starch-based bioplastics," Bioresource Technology, 2010, 101:2007-13, available online Nov. 8, 2009.
Hieber, A., et al., "Detection of Elastin in the Human Fetal Membranes: Proposed Molecular Basis for Elasticity," Placenta, 1997, 18(4):301-12.
Hopkinson, A., et al., "Proteomic Analysis of Amniotic Membrane Prepared for Human Transplantation: Characterization of Proteins and Clinical Implications," J Proteome Res, 2006, 5(9):2226-35.
Hsu, G.., "Utilizing Dehydrated Human Amnion/Chorion Membrane Allograft in Transcanal Typanoplasty," Otolaryngology, 2014, 4: 161. doi:10.4172/2161-119X.1000161, 3 pages.
Hu, D., et al., "Staining Characteristics of Preserved Human Amniotic Membrane," Cornea, 2003, 22(1):37-40.
International Preliminary Report on Patentability for International Application No. PCT/US2016/052314, dated Mar. 20, 2018, 10 pages.
International Preliminary Report on Patentability for International Application No. PCT/US2016/052319, dated Mar. 20, 2018, 10 pages.
International Search Report and Written Opinion of International Application No. PCT/US2016/052314, dated Nov. 30, 2016,19 pages.
International Search Report and Written Opinion of International Application No. PCT/US2016/052319, dated Feb. 12, 2016, 20 pages.
Jacobson, A., et al., "Expression of human hyaluronan synthases in response to external stimuli," Biochem J, 2000, 348(Pt 1):29-35.
John, T., "Human amniotic membrane transplantation: Past, present, and future," Ophthalmol Clin N Am, 2003, 16(1):43-65.
Kanayama, N., et al.,"The Role of Low Molecular Weight Hyaluronic Acid Contained in Wharton's Jelly in Necrotizing Funisitis," Pediatr Res, 1999, 45:510-4, 18 printed pages.
Kandavel, G., et al., "Staining Properties of Deepithelialized Human Amniotic Membrane," Cornea, 2005, 24(7):853-56.
Keene, D., "Type VII Collagen Forms an Extended Network of Anchoring Fibrils," J Cell Biol, 1987, 104(3):611-21.
Klen, R., "Preparation of Chorion and/or amnion grafts used in burns," Transactions of the Third International Congress on Research in Burns, 1970, pp. 289-292.
Koh, J., et al., "The Expression of TIMPs in Cryo-Preserved and Freeze-Dried Amniotic Membrane," Curr Eye Res, 2007, 32(7-8):611-6.
Ambiodisk®, Clearify™ Processed Office Based Amniotic Membrane Grafts, KB-SS-072219 Rev0, (2019) (https://www.katena.com/pub/media/contentmanager/content/literature-pdf/AmbioDisk_Information.pdf) (2 pages).
Katena, AMBIO2® AMBIO5® Clearify™ processed surgical amniotic membrane allografts, KB-SS-071919 Rev1 (2019) (https://199752-598097-raikfcquaxqncofqfm.stackpathdns.com/pub/media/contentmanager/content/literature-pdf/Clearify_Ambio2_Ambio5_Katena.pdf?=bi) (2 pages).
Katena, AMBIO2® and AMBIO5® Allograft Instructions for Use, LBL19-009 Rev 05 (2021) (2 pages).
Katena, AMBIODisk® Allograft Instructions for Use, LBL19-011 Rev 05 (2021) (2 pages).
Katena, Clearify™ Processed Surgical Amniotic Membrane Grafts, AMBIO2® AMBIO5®, KB-SS-071919-Rev0 (2019) (2 pages).

(56) References Cited

OTHER PUBLICATIONS

Revita® Clear Intact Human Placental Membrane, StimLabs, MKTG 19-016 Rev 02 (2021) (1 page).
Revita® Burn & Revita® Burn Clear Allograft Instructions for Use, StimLabs, LBL18-013 Rev 02 (2019) (2 pages).
Revita® Burn & Revita® Burn Clear Allograft Instructions for Use, StimLabs, LBL18-014 Rev 02 (2019) (2 pages).
Revita® Burn Clear Allograft Instructions for Use, StimLabs, LBL18-017 Rev 02 (2019) (2 pages).
Revita® Burn Clear Intact Human Placental Membrane, StimLabs, MKTG 19-013 Rev 03 (2021) (1 page).
Revita® Burn Clear Intact Human Placental Membrane, StimLabs, MKTG 19-015 Rev 01 (2019) (1 page).
Revita® Clear A Next Generation Human Placental Allograft, StimLabs, MKTG 19-001 Rev 02 (2021) (1 page).
Revita® Clear Allograft Instructions for Use Dehydrated Human Placental Tissue Allograft, StimLabs, LBL17-033 Rev 02 (2019) (2 pages).
Revita® Clear Allograft Instructions for Use Dehydrated Human Placental Tissue Allograft, StimLabs, LBL17-034 Rev 02 (2019) (2 pages).
Revita® Clear Full-Thickness Barrier Membrane, StimLabs, MKTG 20-002 Rev 02 (2020) (2 pages).
Image File Wrapper of U.S. Appl. No. 17/486,642, filed Sep. 27, 2021.
Vishwakarma, G., et al., "Amniotic Arthroplasty for Tuberculosis of the Hip," J Bone Joint Surg Br, 1986, 68(1):68-74.
Visse, R. & Nagase, H., "Matrix Metalloproteinases and Tissue Inhibitors of Metalloproteinases: Structure, Function, and Biochemistry," Circ Res, 2003, 92(8):827-39 and Supplementary Data pp. 1-9.
Werner, S. & Grose, R., "Regulation of Wound Healing by Growth Factors and Cytokines," Physiol Rev., 2003, 83(3):835-70.
Zebardast, N., et al., "Human umbilical cord perivascular cells (HUCPVC): A mesenchymal cell source for dermal wound healing," Organogenesis, 2010, 6(4):197-203.
Zelen, C., et al., "A prospective, randomised, controlled, multi-centre comparative effectiveness study of healing using dehydrated human amnion/chorion membrane allograft, bioengineered skin substitute or standard of care for treatment of chronic lower extremity diabetic ulcers," Int Wound J, 2015, 12(6):724-32.
Revita™ The First Full Thickness Placental Membrane Allograft, LBL16-014 Rev 01 (2016) (2 pages).
Revita™ Intact Human Placental Membrane, LBL16-012 Rev 01 (2016) (1 page).
StimLabs Enters Regenerative Medicine Market with Two Ground-breaking Amniotic Tissue Products, Jul. 25, 2017, 2 pages (accessed from https://www.prnewswire.com/news-releases/stimlabs-enters-regenerative-medicine-market-with-two-groundbreaking-amniotic-tissue-products-300493787.html on Aug. 4, 2021) (3 pages).
Amendment and Response filed under 37 CFR 1.114, RCE, amended specification, and Declaration of Dr. Sarah Griffiths Under 37 CFR 1.132 for U.S. Appl. No. 15/760,757, filed May 12, 2022.
Notice of Allowance for U.S. Appl. No. 15/760,757, dated Jun. 2, 2022.
Amendment and Response filed under 37 CFR 1.114, RCE, amended specification, and Declaration of Dr. Sarah Griffiths Under 37 CFR 1.132 for U.S. Appl. No. 15/739,567, filed Jun. 15, 2022.
Non-Final Office Action for U.S. Appl. No. 15/739,567, dated Jul. 6, 2022.
Examiner Interview Summary for U.S. Appl. No. 15/739,567, dated Aug. 9, 2022.
Amendment and Response to Non-Final Office Action for U.S. Appl. No. 15/739,567, filed Aug. 22, 2022.
Image File Wrapper of U.S. Pat. No. 11,559,553, issued Jan. 24, 2023.
Image File Wrapper of U.S. Appl. No. 17/858, 146, filed Jul. 6, 2022.
Image File Wrapper of U.S. Pat. No. 11,413,372, issued Aug. 16, 2022.
RayBio® Human Hemoglobin ELISA Kit, RayBiotech, Catalog #: ELH-Hgb, User Manual, Last revised Jun. 14, 2021 (12 pages).
RayBio® Human Hemoglobin ELISA Kit, RayBiotech, Catalog #: ELH-Hgb, User Manual, Last revised Dec. 7, 2015 (12 pages).
RayBio® Human Hemoglobin ELISA Kit, RayBiotech, Catalog #: ELH-Hgb, User Manual, Last revised Jan. 29, 2021 (12 pages).
RayBio® Human Hemoglobin ELISA Kit, RayBiotech, Catalog #: ELH-Hgb, User Manual, Last revised Jul. 6, 2017 (12 pages).

* cited by examiner

TRANSLUCENT, DEHYDRATED PLACENTAL TISSUE AND METHODS OF PRODUCING AND USING THE SAME

CROSS-REFERENCE TO RELATED APPLICATIONS

This application is a continuation of U.S. application Ser. No. 16/225,733, filed Dec. 19, 2018, which claims the benefit of priority to U.S. Provisional Application No. 62/609,771, filed Dec. 22, 2017, which is incorporated by reference herein in its entirety for any purpose.

FIELD

This application relates to methods of dehydrating placental tissue to produce translucent, dehydrated placental tissue for use in wound healing or other clinical applications.

BACKGROUND

Preservation for long-term storage of placental tissue is crucial for use in wound healing and other medical applications. Current methods of preserving tissue and prolonging the tissue shelf-life include heat drying, desiccating, chemical dehydration, freeze-drying, and cryopreserving. Current methods of preservation each bestow unique qualities to tissue, including changes to appearance, altered biomechanical properties, changes to handling characteristics, altered molecular compositions, and changes to the way tissues can behave in vivo and in vitro. The way a preservation method may affect a tissue is thought to vary depending on the type of tissue and its composition.

This application provides for compositions comprising repeatedly dehydrated placental tissues (e.g., placental membranes and umbilical cord) and details methods of preparing and using those compositions. The molecular structures and interactions of placental tissues, including unseparated amnion/chorion tissue, separated amnion and intermediate layer, separated chorion and intermediate layer, and umbilical cord, pose a challenge to drying. For example, intermediate layer of placental membranes and Wharton's Jelly of umbilical cord are understood to include a complex extracellular matrix of specialized proteins and other biomolecules (e.g., glycosaminoglycans, proteoglycans, hyaluronic acid, etc.). Extracellular matrix proteins and biomolecules may contribute to the visual characteristics observed after tissue is dried. For example, oven dehydrated placental tissues can feel brittle, appear opaque, and/or appear uneven with visible white patches and/or striations. Such characteristics are less desirable for some medical applications. There is a need for a dehydration method that produces translucent, dehydrated placental tissue that does not involve removing intermediate layer or Wharton's Jelly.

Since the early 1900s, grafts derived from placental membranes have been used in skin transplantation, such as wound dressings, patch grafts, and in the management of burns and ulcers. Placental membrane grafts have also been used in a variety of other procedures, including tympanoplasty, arthroplasty, in the reconstruction of the oral cavity, bladder, vagina, in the regeneration of the ocular surface and peripheral nerves, and in wound coverings in dental surgery. More recently, similar uses have been found for grafts derived from umbilical cord tissue. Umbilical cord derived grafts have been used as scaffolds for tissue engineering, as wound dressings to treat ulcers, and as adhesion barriers.

The placenta includes the amniotic sac, which develops from extraembryonic tissue and separates the developing fetus from the maternal endometrium. The amniotic sac includes a thin but resilient pair of membranes—the amnion and the chorion—separated by an intermediate (or spongy) layer. The amnion is the innermost membrane of the amniotic sac and is in contact with the amniotic fluid, the fetus, and the umbilical cord. The chorion, which is loosely connected to the intermediate layer, forms the outermost layer of the amniotic sac separating the amnion from the maternal endometrium. The chorion is generally several times thicker than the amnion, but the amnion is understood to be stronger and stiffer than the chorion. The amnion and chorion interface at the intermediate layer, which is a spongy layer that is rich in extracellular matrix proteins and other biomolecules. The umbilical cord connects the fetus to the placenta and allows the transfer of nutrients from the mother to the fetus. The umbilical cord is composed of a single umbilical vein and two umbilical arteries, which span between the placenta and the fetus. These vessels are surrounded by a thick layer of extracellular matrix called Wharton's Jelly, which contains a high amount of proteoglycans. Wharton's Jelly is a gelatinous substance that insulates the vessels of the umbilical cord. The vessels and Wharton's Jelly are wrapped in a layer of amnion that is contiguous with the amnion of the placental membranes. Niknejad, H., et al., Properties of the amniotic membrane for potential use in tissue engineering. *European Cells and Materials* 15, 88-99 (2008). Sobolewski, K., et al., Collagen and Glycosaminoglycans of Wharton's Jelly. *Biology of the Neonate* 71, 11-21 (1997).

Placental membranes and the umbilical cord are complicated tissues composed of numerous components, such as extracellular matrix molecules, cells, growth factors, and other biomolecules. These tissues are understood to possess many biological properties important for tissue regeneration and wound healing, such as promotion of cell migration and growth; low immunogenicity; and anti-fibrosis, anti-scarring, anti-microbial, anti-inflammatory, and anti-pain activities. Placental membranes and umbilical cord tissue may also serve as a scaffold for cell proliferation and differentiation.

The vast majority of the extracellular matrix of intermediate layer and of Wharton's Jelly is proteoglycans and glycosaminoglycans. Glycosaminoglycans are hydrophilic and bind water, and therefore play an important role in synovial fluid and soft tissue as shock absorbers and lubricants. Proteoglycans are proteins that are covalently bonded to glycosaminoglycans, and are understood to play an important structural role in the extracellular matrix and provide a hydrating environment between cells that may allow for the movement of molecules through the matrix. Glycosaminoglycans and proteoglycans may also lend additional firmness, elasticity, and strength to tissues. Glycosaminoglycans and proteoglycans are also understood to play an important role in the different stages of the wound healing cascade. Bryant-Greenwood, G D. The Extracellular Matrix of the Fetal Membranes: Structures and Function. *Placenta* 19, 1-11 (1998). Meinert, M., et al., Proteoglycans and hyaluronan in human fetal membranes. *American Journal of Obstetrics and Gynecology* 184, 679-685 (2001).

Often, current methods of preparing translucent placental membrane grafts involve manually separating the amnion from the chorion to allow access to and removal of blood remnants. When the amnion and chorion are separated, the intermediate layer or the reticular layer of the chorion are exposed. Even gentle washing of separated amnion or separated chorion may result in removal of the intermediate layer. In many cases, the intermediate layer is purposefully removed to reduce the amount of blood remnants. Removal of the intermediate layer results in the loss of membrane components important to tissue regeneration and wound healing, including cytokines, growth factors, other regulatory factors, and extracellular matrix molecules, such as glycosaminoglycans and proteoglycans. Furthermore, a thin separated amnion can be difficult to position during transplantation, may tend to roll up on itself during transplantation, or may be difficult to secure in place with sutures.

Current methods of dehydration do not allow for the preparation of a translucent, dehydrated placental membrane with intermediate layer or a translucent, dehydrated umbilical cord with Wharton's Jelly. Freeze-drying methods applied to placental tissues with intermediate layer or Wharton's Jelly produce a dehydrated tissue that is relatively pliable, but opaque. Attempts to dehydrate placental tissues with intermediate layer or Wharton's Jelly according to other standard dehydration techniques used in the field, such as oven dehydration, produce dehydrated tissues that are opaque or brittle. As discussed, placental tissues with intermediate layer or Wharton's Jelly are advantageous for use in the wound healing process. Dehydrated placental tissues with intermediate layer or Wharton's Jelly that are translucent are advantageous for wound healing, including ophthalmic, dental, and burn applications. For example, translucency may allow a medical professional to observe a wound through the dehydrated tissue and allow for easier positioning of the tissue on the wound. Thus, there is a need for a method of producing translucent, dehydrated placental tissues, including those having enhanced handling characteristics (e.g., thickness, strength, and pliability).

SUMMARY

Embodiment 1. A dehydrated placental tissue comprising an intermediate layer and/or Wharton's Jelly, wherein the dehydrated placental tissue is translucent.

Embodiment 2. The dehydrated placental tissue of embodiment 1, wherein the dehydrated placental tissue, a portion of the dehydrated placental tissue, substantially all of the dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or at least 80% of the placental tissue allows substantially all visible light to pass through.

Embodiment 3. The dehydrated placental tissue of embodiment 1 or embodiment 2, wherein the dehydrated placental tissue, a portion of the dehydrated placental tissue, substantially all of the dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or at least 80% of the placental tissue appears translucent by visual inspection.

Embodiment 4. The dehydrated placental tissue of any one of the preceding embodiments, wherein the dehydrated placental tissue, a portion of the dehydrated placental tissue, substantially all of the dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of the placental tissue appears translucent by visual inspection, as determined by holding the dehydrated placental tissue between a visible light source and a surface having marking(s) and visually detected whether the marking(s) on the surface are visible through the tissue.

Embodiment 5. The dehydrated placental tissue of any one of the preceding embodiments, wherein the dehydrated placental tissue, a portion of the dehydrated placental tissue, substantially all of the dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of the placental tissue has a light transmission of from 5% to 90%, such as 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% or less than a value listed above, greater than a value listed above, at least a value listed above, or a range of values bounded by any two of the values listed above, such as 10% to 90%, 10% to 85%, 10% to 80%, 15% to 20%, 30% to 35%, 35% to 40%, 30% to 45%, 35% to 50%, 70% to 80%, 45% to 55%, 50% to 90%, 50% to 85%, 60% to 90%, 60% to 85%, 65% to 80%, 75% to 90%, 75% to 85%, 55% to 60%, or 40% to 50%, as determined by spectrophotometry at a wavelength of from 360 nm to 750 nm, such as at a wavelength of 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, and/or 750 nm, or less than a wavelength listed above, greater than a wavelength listed above, at least a wavelength listed above, or a range of wavelengths, such as from 370 nm to 400 nm, 370 nm to 750 nm, 390 nm to 700 nm, 500 nm to 750 nm, or 500 nm to 700 nm.

Embodiment 6. The dehydrated placental tissue of any one of the preceding embodiments, wherein the dehydrated placental tissue, a portion of the dehydrated placental tissue, substantially all of the dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of the placental tissue has a light transmission of greater than 60% as determined by spectrophotometry at a wavelength of 360 nm, 370 nm, 380 nm, 390 nm, 400 nm, and/or 410 nm.

Embodiment 7. The dehydrated placental tissue of any one of the preceding embodiments, wherein the dehydrated placental tissue, a portion of the dehydrated placental tissue, substantially all of the dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of the placental tissue has a light transmission of greater than 80% as determined by spectrophotometry at a wavelength ranging from 580 nm to 750 nm, and/or at a wavelength of 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, and/or 750 nm.

Embodiment 8. The dehydrated placental tissue of any one of the preceding embodiments, wherein the dehydrated placental tissue is from a human donor.

Embodiment 9. The dehydrated placental tissue of any one of the preceding embodiments, wherein the dehydrated placental tissue comprises unseparated amnion/chorion, amnion, chorion, unseparated umbilical cord, separated umbilical cord, and/or umbilical cord amnion.

Embodiment 10. The dehydrated placental tissue of any one of the preceding embodiments, wherein the dehydrated placental tissue comprises a substantial amount of intermediate layer.

Embodiment 11. The dehydrated placental tissue of any one of the preceding embodiments, wherein the dehydrated placental tissue comprises an intermediate layer having a mean thickness of from 1 µm to 200 µm, of from 1 µm to 150 µm, of from 5 µm to 200 µm, of from 10 µm to 150 µm, of greater than 1 µm, of greater than 5 µm, or of greater than 10 µm.

Embodiment 12. The dehydrated placental tissue of any one of the preceding embodiments, wherein the dehydrated placental tissue comprises a substantial amount of Wharton's Jelly.

Embodiment 13. The dehydrated placental tissue of any one of the preceding embodiments, wherein the dehydrated placental tissue is substantially free of blood remnants.

Embodiment 14. The dehydrated placental tissue of any one of the preceding embodiments, wherein the dehydrated placental tissue has a hemoglobin content of less than 13 ng/mg, less than 10 ng/mg, less than 5 ng/mg, less than 1 ng/mg, or less than 0.5 ng/mg of dry mass of the tissue.

Embodiment 15. The dehydrated placental tissue of any one of the preceding embodiments, wherein the dehydrated placental tissue has a moisture content of 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 20%, 25%, 30%, 35%, 40%, 45%, 50%, or less than any percentage listed above, greater than any percentage listed above, at least any percentage listed above, or a range of percentages bounded by any two of the percentages listed above, such as 0.5% to 50%, 0.5% to 0.9%, 1% to 2%, 2% to 3%, 3% to 5%, 5% to 7%, 7% to 10%, 10% to 12%, 12% to 15%, 0.5% to 5%, 5% to 10%, 10% to 15%, 2% to 4%, 4% to 6%, 6% to 8%, 8% to 10%, 1% to 15%, 1% to 10%, 10% to 20%, 10% to 30%, 20% to 30%, or 30% to 50%.

Embodiment 16. The dehydrated placental tissue of any one of the preceding embodiments, wherein the dehydrated placental tissue appears dry or feels dry to the touch.

Embodiment 17. The dehydrated placental tissue of any one of the preceding embodiments, wherein the dehydrated placental tissue is sterile.

Embodiment 18. The dehydrated placental tissue of any one of the preceding embodiments, wherein the dehydrated placental tissue is perforated.

Embodiment 19. A method of preparing a dehydrated placental tissue comprising:
a) a first dehydration step comprising dehydrating a placental tissue using at least one dehydration technique, and
b) a final dehydration step comprising dehydrating the placental tissue using at least one dehydration technique comprising air drying, wherein the dehydrated placental tissue is produced as a result of the final dehydration step.

Embodiment 20. The method of embodiment 19, wherein at least one dehydration technique used in the first dehydration step and at least one dehydration technique used in the final dehydration step are different.

Embodiment 21. The method of embodiment 19, wherein at least one dehydration technique used in the first dehydration step and at least one dehydration technique used in the final dehydration step are the same.

Embodiment 22. The method of any one of embodiments 19 to 21, wherein the method comprises a second dehydration step, a third dehydration step, a fourth dehydration step, a fifth dehydration step, a sixth dehydration step, a seventh dehydration step, and/or an eighth dehydration step before the final dehydration step.

Embodiment 23. The method of embodiment 22, wherein the first, second, third, fourth, fifth, sixth, seventh, and/or eighth dehydration step comprises dehydrating a placental tissue using at least one dehydration technique comprising chemical dehydration, air drying, and/or freeze drying.

Embodiment 24. The method of any one of embodiments 19 to 23, wherein at least one dehydration technique comprises freeze drying.

Embodiment 25. The method of any one of embodiments 19 to 24, wherein at least one dehydration technique comprises chemical dehydration.

Embodiment 26. The method of any one of embodiments 19 to 25, wherein at least one dehydration technique comprises air drying.

Embodiment 27. The method of any one of embodiments 19 to 26, wherein at least one dehydration technique comprises air drying, and wherein air drying comprises oven drying, drying with heated air, drying at ambient temperature, drying with cycled air, drying with convection, and/or desiccation.

Embodiment 28. The method of any one of embodiments 19 to 27, wherein the air drying is performed under a vacuum.

Embodiment 29. The method of any one of embodiments 19 to 28, wherein the placental tissue is hydrated between any two dehydration steps.

Embodiment 30. The method of embodiment 29, wherein the placental tissue is hydrated between a first dehydration step and a second dehydration step, between a second dehydration step and a third dehydration step, between a third dehydration step and a fourth dehydration step, between a fourth dehydration step and a fifth dehydration step, between a fifth dehydration step and a sixth dehydration step, between a sixth dehydration step and a seventh dehydration step, and/or between a seventh dehydration step and an eighth dehydration step.

Embodiment 31. A method of preparing a dehydrated placental tissue comprising:
a) dehydrating a placental tissue in a first dehydration environment;
b) hydrating the placental tissue in a hydration environment; and
c) dehydrating the placental tissue in a second dehydration environment.

Embodiment 32. The method of any one of embodiments 19 to 31, wherein the dehydrated placental tissue is translucent.

Embodiment 33. The method of any one of embodiments 19 to 32, wherein the dehydrated placental tissue, a portion of the dehydrated placental tissue, substantially all of the dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or at least 80% of the placental tissue allows substantially all visible light to pass through.

Embodiment 34. The method of any one of embodiments 19 to 33, wherein the dehydrated placental tissue, a portion of the dehydrated placental tissue, substantially all of the dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or at least 80% of the placental tissue appears translucent by visual inspection.

Embodiment 35. The method of any one of embodiments 19 to 34, wherein the dehydrated placental tissue, a portion of the dehydrated placental tissue, substantially all of the dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or at least 80% of the placental tissue appears translucent by visual inspection, as determined by holding the dehydrated placental tissue between a visible light source and a surface having marking(s) and visually detected whether the marking(s) on the surface are visible through the tissue.

Embodiment 36. The method of any one of embodiments 19 to 35, wherein the dehydrated placental tissue, a portion of the dehydrated placental tissue, substantially all of the dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or at least 80% of the placental tissue has a light transmission of from 5% to 90%, such as 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% or less than a value listed above, greater than a value listed above, at least a value listed above, or a range of values bounded by any two of the values listed above, such as 10% to 90%, 10% to 85%, 10% to 80%, 15% to 20%, 30% to 35%, 35% to 40%, 30% to 45%, 35% to 50%, 70% to 80%, 45% to 55%, 50% to 90%, 50% to 85%, 60% to 90%, 60% to 85%, 65% to 80%, 75% to 90%, 75% to 85%, 55% to 60%, or 40% to 50%, as determined by spectrophotometry at a wavelength of from 360 to 750 nm, such as at a wavelength of 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, and/or 750 nm, or less than a wavelength listed above, greater than a wavelength listed above, at least a wavelength listed above, or a range of wavelengths, such as from 370 nm to 400 nm, 370 nm to 750 nm, 390 nm to 700 nm, 500 nm to 750 nm, or 500 nm to 700 nm.

Embodiment 37. The dehydrated placental tissue of any one of embodiments 19 to 36, wherein the dehydrated placental tissue, a portion of the dehydrated placental tissue, substantially all of the dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of the placental tissue has a light transmission of greater than 60% as determined by spectrophotometry at a wavelength of 360 nm, 370 nm, 380 nm, 390 nm, 400 nm, and/or 410 nm.

Embodiment 38. The dehydrated placental tissue of any one of embodiments 19 to 37, wherein the dehydrated placental tissue, a portion of the dehydrated placental tissue, substantially all of the dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of the placental tissue has a light transmission of greater than 80% as determined by spectrophotometry at a wavelength ranging from 580 nm to 750 nm, and/or at a wavelength of 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, and/or 750 nm.

Embodiment 39. The method of any one of embodiments 19 to 38, wherein the placental tissue and/or the dehydrated placental tissue comprises proteoglycans and/or glycosaminoglycans.

Embodiment 40. The method of any one of embodiments 19 to 39, wherein the placental tissue and/or the dehydrated placental tissue comprises hyaluronic acid.

Embodiment 41. The method of any one of embodiments 19 to 40, wherein the placental tissue and/or the dehydrated placental tissue is from a human donor.

Embodiment 42. The method of any one of embodiments 19 to 41, wherein the placental tissue and/or the dehydrated placental tissue comprises a placental membrane and/or an umbilical cord.

Embodiment 43. The method of any one of embodiments 19 to 42, wherein the placental tissue and/or the dehydrated placental tissue comprises unseparated amnion/chorion, amnion, chorion, unseparated umbilical cord, separated umbilical cord, and/or umbilical cord amnion.

Embodiment 44. The method of any one of embodiments 19 to 43, wherein the placental tissue and/or the dehydrated placental tissue comprises an intermediate layer.

Embodiment 45. The method of any one of embodiments 19 to 44, wherein the placental tissue and/or the dehydrated placental tissue comprises a substantial amount of intermediate layer.

Embodiment 46. The method of any one of embodiments 19 to 45, wherein the placental tissue and/or the dehydrated placental tissue comprises an intermediate layer having a mean thickness of from 1 μm to 200 μm, of from 1 μm to 150 μm, of from 5 μm to 200 μm, of from 10 μm to 150 μm, of greater than 1 μm, of greater than 5 μm, or of greater than 10 μm.

Embodiment 47. The method of any one of embodiments 19 to 46, wherein the placental tissue and/or the dehydrated placental tissue comprises Wharton's Jelly.

Embodiment 48. The method of any one of embodiments 19 to 47, wherein the placental tissue and/or the dehydrated placental tissue comprises a substantial amount of Wharton's Jelly.

Embodiment 49. The method of any one embodiments 19 to 48, wherein the placental tissue and/or the dehydrated placental tissue is substantially free of blood remnants.

Embodiment 50. The method of any one of embodiments 19 to 49, wherein the placental tissue and/or the dehydrated placental tissue has a hemoglobin content of less than 13 ng/mg, less than 10 ng/mg, less than 5 ng/mg, less than 1 ng/mg, or less than 0.5 ng/mg of dry mass of the tissue.

Embodiment 51. The method of any one of embodiments 19 to 50, wherein the placental tissue and/or the dehydrated placental tissue is perforated.

Embodiment 52. The method of any one of embodiments 19 to 51, wherein at least one dehydration technique comprises using a dehydration environment having a temperature of, or at least one dehydration environment has a temperature of from 15° C. to 70° C., such as 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48°

C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., or 70° C. or less than a value listed above, greater than a value listed above, at least a value listed above, or a range of values bounded by any two of the values listed above, such as 15° C. to 20° C., 32° C. to 34° C., 35° C. to 36° C., 32° C. to 43° C., 34° C. to 38° C., 61° C. to 69° C., 45° C. to 51° C., 56° C. to 7° C., 55° C. to 59° C., 41° C. to 47° C., 20° C. to 40° C., 30° C. to 50° C., or 40° C. to 60° C.

Embodiment 53. The method of any one of embodiments 19 to 52, wherein at least one dehydration technique comprises using a dehydration environment having a vacuum pressure of, or at least one dehydration environment has a vacuum pressure of from 0.0001 in Hg to 25 in Hg, such as 0.0001 inHg, 0.0005 in Hg, 0.001 in Hg, 0.005 in Hg, 0.01 in Hg, 0.05 in Hg, 0.1 in Hg, 0.2 in Hg, 0.3 in Hg, 0.4 in Hg, 0.5 in Hg, 0.6 in Hg, 0.7 in Hg, 0.8 in Hg, 0.9 in Hg, 1 in Hg, 2 in Hg, 3 in Hg, 4 in Hg, 5 in Hg, 6 in Hg, 7 in Hg, 8 in Hg, 9 in Hg, 10 in Hg, 11 in Hg, 12 in Hg, 13 in Hg, 14 in Hg, 15 in Hg, 16 in Hg, 17 in Hg, 18 in Hg, 19 in Hg, 20 in Hg, 21 in Hg, 22 in Hg, 23 in Hg, 24 in Hg, 25 in Hg, or less than a value listed above, greater than a value listed above, at least a value listed above, or a range of values bounded by any two values listed above, such as 0.0001 in Hg to 0.001 in Hg, 0.001 in Hg to 0.01 in Hg, 0.01 in Hg to 0.1 in Hg, 0.1 in Hg to 1 in Hg, 1 in Hg to 5 in Hg, 1 in Hg to 10 in Hg, 1 in Hg to 20 in Hg, 1 in Hg to 25 in Hg, 0.1 in Hg to 20 in Hg, or 0.01 in Hg to 1 in Hg.

Embodiment 54. The method of any one of embodiments 19 to 53, wherein at least one dehydration technique comprises using a dehydration environment having a temperature of, or at least one dehydration environment has a temperature of from −100° C. to 0° C., such as −100° C., −99° C., −98° C., −97° C., −96° C., −95° C., −94° C., −93° C., −92° C., −91° C., −90° C., −89° C., −88° C., −87° C., −86° C., −85° C., −84° C., −83° C., −82° C., −81° C., −80° C., −79° C., −78° C., −77° C., −76° C., −75° C., −74° C., −73° C., −72° C., −71° C., −70° C., −69° C., −68° C., −67° C., −66° C., −65° C., −64° C., −63° C., −62° C., −61° C., −60° C., −59° C., −58° C., −57° C., −56° C., −55° C., −54° C., −53° C., −52° C., −51° C., −50° C., −49° C., −48° C., −47° C., −46° C., −45° C., −44° C., −43° C., −42° C., −41° C., −40° C., −39° C., −38° C., −37° C., −36° C., −35° C., −34° C., −33° C., −32° C., −31° C., −30° C., −29° C., −28° C., −27° C., −26° C., −25° C., −24° C., −23° C., −22° C., −21° C., −20° C., −19° C., −18° C., −17° C., −16° C., −15° C., −14° C., −13° C., −12° C., −11° C., −10° C., −9° C., −8° C., −7° C., −6° C., −5° C., −4° C., −3° C., −2° C., −1° C., or 0° C. or less than a value listed above, greater than a value listed above, at least a value listed above, or a range of values bounded by any two of the values listed above, such as −90° C. to −10° C., −100° C. to −80° C., −80° C. to −60° C., −70° C. to −40° C., −60° C. to −30° C., −20° C. to 0° C., −50° C. to 0° C., −80° C. to −40° C., or −32° C. to −10° C.

Embodiment 55. The method of any one of embodiments 19 to 54, wherein at least one dehydration technique comprises using a dehydration environment having a vacuum pressure of, or at least one dehydration environment has a vacuum pressure of from 1 µbar to 65 mbar, such as 1 µbar, 10 µbar, 20 µbar, 30 µbar, 40 µbar, 50 µbar, 60 µbar, 70 µbar, 80 µbar, 90 µbar, 100 µbar, 200 µbar, 300 µbar, 400 µbar, 500 µbar, 600 µbar, 700 µbar, 800 µbar, 900 µbar, 1 mbar, 2 mbar, 3 mbar, 4 mbar, 5 mbar, 6 mbar, 7 mbar, 8 mbar, 9 mbar, 10 mbar, 11 mbar, 12 mbar, 13 mbar, 14 mbar, 15 mbar, 16 mbar, 17 mbar, 18 mbar, 19 mbar, 20 mbar, 21 mbar, 22 mbar, 23 mbar, 24 mbar, 25 mbar, 26 mbar, 27 mbar, 28 mbar, 29 mbar, 30 mbar, 31 mbar, 32 mbar, 33 mbar, 34 mbar, 35 mbar, 36 mbar, 37 mbar, 38 mbar, 39 mbar, 40 mbar, 41 mbar, 42 mbar, 43 mbar, 44 mbar, 45 mbar, 46 mbar, 47 mbar, 48 mbar, 49 mbar, 50 mbar, 51 mbar, 52 mbar, 53 mbar, 54 mbar, 55 mbar, 56 mbar, 57 mbar, 58 mbar, 59 mbar, 60 mbar, 61 mbar, 62 mbar, 63 mbar, or 64 mbar, or 65 mbar, or less than a value listed above, greater than a value listed above, at least a value listed above, or a range of values bounded by any two values listed above, such as from 1 µbar to 100 µbar, 1 µbar to 20 µbar, 1 µbar to 50 µbar, 30 µbar to 100 µbar, 50 µbar to 150 µbar, 1 µbar to 1 mbar, 500 µbar to 5 mbar, 1 mbar to 20 mbar, 5 mbar to 50 mbar, 1 mbar to 65 mbar, or 15 mbar to 50 mbar.

Embodiment 56. The method of any one of embodiments 32 to 55, wherein the temperature of at least one dehydration environment and/or the pressure of at least one dehydration environment changes over time.

Embodiment 57. The method of any one of embodiments 32 to 55, wherein the temperature of at least one dehydration environment and/or the pressure of at least one dehydration environment does not change over time.

Embodiment 58. The method of any one of embodiments 19 to 57, wherein at least one dehydration step lasts a period of time of, or the tissue is in at least one dehydration environment for a period of time of from 5 minutes to 120 hours, such as 5 minutes, 15 minutes, 30 minutes, 1 hour, 2 hours, 3 hours, 4 hours, 6 hours, 7 hours, 8 hours, 12 hours, 15 hours, 18 hours, 20 hours, 24 hours, 30 hours, 36 hours, 42 hours, 48 hours, 54 hours, 60 hours, 66 hours, 72 hours, 78 hours, 84 hours, 90 hours, 96 hours, 102 hours, 108 hours, 114 hours, or 120 hours, or less than any value listed above, greater than any value listed above, at least any value listed above, or a range of values bounded by any two of the values listed above, such as 5 minutes to 1 hour, 1 hour to 4 hours, 1 hour to 8 hours, 4 hours to 15 hours, 15 hours to 18 hours, 4 hours to 36 hours, 8 hours to 24 hours, 15 hours to 20 hours, 18 hours to 24 hours, 24 hours to 36 hours, 4 hours to 72 hours, 24 hours to 120 hours, 66 hours to 120 hours, 96 hours to 120 hours, or 18 hours to 120 hours.

Embodiment 59. The method of any one of embodiments 19 to 58, wherein at least one dehydration technique comprises chemical dehydration with a medium, or at least one dehydration environment is a medium, wherein the medium comprises an alcohol, an organic solvent, a hydrophilic polymer, and/or a salt.

Embodiment 60. The method of any one of embodiments 19 to 59, wherein the placental tissue is hydrated between any two dehydration steps in a hydration environment comprising a hydration medium comprising water, saline, phosphate buffer, and/or cell culture media.

Embodiment 61. The method of any one of embodiments 19 to 60, wherein the placental tissue is hydrated between any two dehydration steps in a hydration environment comprising a hydration medium selected from water, a sodium chloride solution, a sodium hypochlorite solution, a hydrogen peroxide solution, Lactated Ringer's solution, Ringer's solution, phosphate-buffered saline (PBS), tris-buffered saline (TBS), Hank's balanced salt solution (HBSS), Dulbecco's phosphate-buffered saline (DPBS), Earle's balanced salt solution (EBSS), standard saline citrate (SSC), HEPES-buffered saline (HBS), Gey's balanced salt solution (GB SS), Delbecco's Modified Eagle Medium (DMEM), and Minimum Essential Media (MEM).

Embodiment 62. The method of any one of embodiments 19 to 61, wherein the placental tissue is hydrated between any two dehydration steps in a hydration environment comprising a hydration medium comprising one or more ingredients selected from phosphate, potassium, magnesium, calcium, dextrose, glucose, citrate, lactate, TRIS, and HEPES.

Embodiment 63. The method of any one of embodiments 19 to 62, wherein the placental tissue is hydrated between any two dehydration steps by soaking in a hydration medium with or without agitation.

Embodiment 64. The method of any one of embodiments 19 to 63, wherein the placental tissue is hydrated between any two dehydration steps by soaking the placental tissue in a hydration medium with agitation using a rocker, shaker, stir plate, or rotating mixer.

Embodiment 65. The method of any one of embodiments 19 to 64, wherein the placental tissue is hydrated between any two dehydration steps for a time period of from 1 second to 72 hours, such as 1 second, 30 seconds, 1 minute, 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 64 hours, and 72 hours, or for a time period time less than any of the time periods listed above, greater than any of the time periods listed above, of at least any of the time periods listed above, or a range bounded by any two of the time periods listed above, such as 1 second to 5 minutes, 5 minutes to 20 minutes, 5 minutes to 1 hour, 1 hour to 2 hours, 30 minutes to 2 hours, 2 hours to 4 hours, 8 hours to 24 hours, 40 minutes to 12 hours, or 6 hours to 72 hours.

Embodiment 66. The method of any one of embodiments 19 to 65, wherein at least one dehydration technique or at least one dehydrating step reduces the moisture content of the placental tissue by 99.9%, 99.8%, 99.7%, 99.6%, 99.5%, 99.4%, 99.3%, 99.2%, 99.1%, 99%, 98.5%, 98%, 97%, 96%, 95%, 94%, 93%, 92%, 93%, 92%, 91%, 90%, 85%, 80%, 75%, 70%, 65%, 60%, 55%, 50%, 45%, 40%, 35%, 30%, 25%, 20%, 15%, 10%, or 5%, or less than a value listed above, greater than a value listed above, at least a value listed above, or a range of values bounded by any two of the values listed above, such as 99.9% to 99%, 99.5% to 99%, 99% to 95%, 95% to 90%, 95% to 85%, 99% to 90%, 95% to 80%, 95% to 75%, 95% to 50%, 75% to 25%, 50% to 25%, 95% to 25%, or 50% to 10%.

Embodiment 67. The method of any one of embodiments 19 to 66, wherein the dehydrated placental tissue has a moisture content of 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 20%, 25%, 30%, 35%, 40%, 45%, 50%, or less than any percentage listed above, greater than any percentage listed above, at least any percentage listed above, or a range of percentages bounded by any two of the percentages listed above, such as 0.5% to 50%, 0.5% to 0.9%, 1% to 2%, 2% to 3%, 3% to 5%, 5% to 7%, 7% to 10%, 10% to 12%, 12% to 15%, 0.5% to 5%, 5% to 10%, 10% to 15%, 2% to 4%, 4% to 6%, 6% to 8%, 8% to 10%, 1% to 15%, 1% to 10%, 10% to 20%, 10% to 30%, 20% to 30%, or 30% to 50%.

Embodiment 68. The method of any one of embodiments 19 to 67, wherein the dehydrated placental tissue appears dry or feels dry to the touch.

Embodiment 69. A dehydrated placental tissue prepared by the method of any one of embodiments 19 to 68.

Embodiment 70. A composition comprising the dehydrated placental tissue of any one of embodiments 1 to 18 or embodiment 69.

Embodiment 71. A method of treating or covering a wound of a subject comprising applying the dehydrated placental tissue of any one of embodiments 1 to 18 or embodiment 69 or the composition of embodiment 70 to the wound of the subject.

Embodiment 72. The method of embodiment 71, wherein the wound is a wound of the eye, a wound of the skin, a wound of a nerve, a wound of a tendon, a wound of the dura, a periodontal wound, a wound of the abdomen, or a wound of an internal organ.

Embodiment 73. The method of embodiment 72, wherein the eye wound is a burn, a laceration, a corneal ulceration, a conjunctival lesion, or a surgical wound.

Embodiment 74. The method of any one of embodiments 71 to 73, wherein the wound is a burn, a laceration, a diabetic ulcer, a venous ulcer, an arterial ulcer, a decubitus ulcer, or a surgical wound.

These and other aspects and various embodiments are described more fully below.

DESCRIPTION OF CERTAIN EMBODIMENTS

Figure 1A:
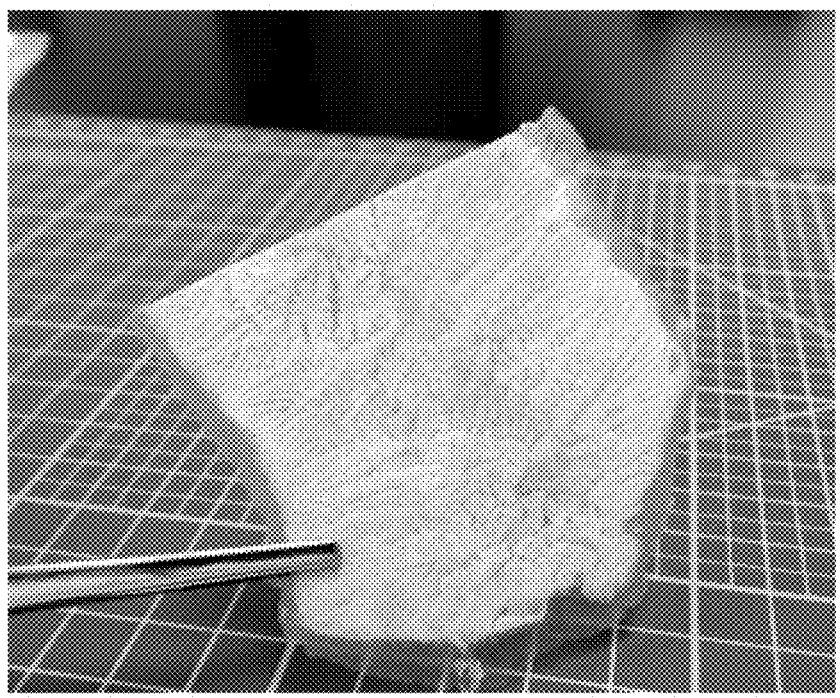
FIG. 1A and FIG. 1B show images of unseparated amnion/chorion after a first oven-dehydration cycle (FIG. 1A), and after hydration followed by a second oven-dehydration cycle FIG. 1B).

The present disclosure provides methods of repeatedly dehydrating placental tissue (e.g., placental membranes and umbilical cord) to produce translucent, dehydrated placental tissue. Translucent, dehydrated placental tissue prepared by the methods described herein, may also possess additional advantageous properties, such as pliability, thickness, and strength. In some embodiments, placental membrane with intermediate layer or umbilical cord with Wharton's Jelly may be repeatedly dehydrated as described herein to produce dehydrated placental tissues having translucency and/or pliability properties more commonly associated with placental tissues lacking intermediate layer or Wharton's Jelly. In addition, the methods described herein allow for the retention of extracellular matrix layers or components (e.g., intermediate layer and Wharton's Jelly) comprising glycosaminoglycans and proteoglycans that may contribute substantially to tissue regeneration and wound healing.

As used herein, "a" or "an" means "at least one" or "one or more" unless specified otherwise. As used herein, the term "or" means "and/or" unless specified otherwise. In the context of a multiple dependent claim, the use of "or" when referring back to other claims refers to those claims in the alternative only.

As used herein, numerical terms are calculated based upon scientific measurements and, thus, are subject to appropriate measurement error. In some instances, a numerical term may include numerical values that are rounded to the nearest significant figure.

In the event that any document or other material incorporated by reference contradicts any explicit content of this specification, including definitions, this specification controls.

I. Exemplary Embodiments of Placental Tissue

As used herein, "placental tissue" refers to a composition comprising layers of cells and extracellular matrix derived from placenta. As used herein, "placenta" refers to any component of the placenta, including amniotic sac, placental disc, and/or umbilical cord, etc. A placental tissue may be collected from a human or other mammal, including but not limited to a primate, artiodactyl, perissodactyl, cow, bison, horse, pig, goat, or the like.

In some embodiments, a placental tissue comprises a placental membrane. In some embodiments, a placental tissue comprises an umbilical cord. In some embodiments, a placental tissue comprises a placental disc. In some embodiments, a placental tissue comprises unseparated amnion/chorion, amnion, chorion, unseparated umbilical cord, separated umbilical cord, and/or umbilical cord amnion. In some embodiments, a placental tissue comprises intermediate layer. In some embodiments, a placental tissue comprises Wharton's Jelly. In some embodiments, a placental tissue comprises proteoglycans or glycosaminoglycans.

Amnion, intermediate layer, and chorion are composed of numerous components, including cells, growth factors, extracellular matrix molecules, and other biomolecules important for tissue regeneration and wound healing. For example, amnion, intermediate layer, or chorion may contain cells, such as epithelial cells, fibroblasts, and trophoblasts; growth factors, such as fibroblast growth factors, epidermal growth factor, transforming growth factor (TGF) beta, platelet-derived growth factors, etc.; extracellular matrix molecules, such as collagens, elastins, proteoglycans, non-proteoglycan polysaccharides, fibronectins, laminins, nidogens, etc.; and other biomolecules, such as cytokines (e.g., interleukins, etc.), metalloproteinases, tissue inhibitors of metalloproteinases (TIMPs), etc.

Amnion consists of four layers: an epithelial monolayer, a basement membrane, a compact layer, and a fibroblast layer. The epithelial layer of the amnion is composed of a single layer of epithelial cells arranged on the basement membrane. Amniotic epithelial cells may include amniotic stem cells or have stem cell-like characteristics. For example, cells of the epithelial layer of the amnion may be capable of differentiating into or producing, in the presence of a differentiation-inducing factor, at least one different cell lineage, such as osteogenic, adipogenic, chondrogenic, myogenic, neurogenic, epithelial, or other cell lineage. Amniotic stem cells or cells with stem cell-like characteristics may also be found in other layers of the amnion or chorion.

Amniotic epithelial cells may lack HLA-A, HLA-B (Class IA) and HA-DR (Class II) on their surfaces suggesting that these cells may be immunologically inert and have reduced risk of rejection or immune reaction upon transplantation.

Amnion/chorion may be processed such that the epithelial layer of the amnion is maintained (intact), partially removed, or substantially removed. The epithelial layer may be removed, for example, by using a mechanical procedure or detergent-based procedure. In one embodiment, epithelial cells are gently scraped away using a cell scraper with the aid of a microscope. In other embodiments, the epithelial layer is removed using an ionic detergent, a non-ionic detergent, or a zwitterionic detergent. In yet a further embodiment, after removal of the epithelial layer, other layers of the amnion/chorion are retained. As used herein, "partially removed" refers to a percentage of the epithelial layer having been removed in the range of 1% to 89% and "substantially removed" refers to a percentage of the epithelial layer having been removed in the range of 90% to 99%. In some embodiments, at least 10%, at least 20%, at least 30%, at least 40%, at least 50%, at least 60%, at least 70%, at least 80%, or at least 90% of the epithelial layer is removed. The base of the epithelial cell layer is in contact with the basement membrane of the amnion. The basement membrane of the amnion is a thin layer comprising extracellular matrix components, including collagen types III, IV, and V, non-collagenous glycoproteins (e.g., laminins, fibronectins, and nidogens), and proteoglycans (e.g., perlecans). The compact layer of the amnion is a dense, fibrous network comprising extracellular matrix components, including collagens (e.g., collagen types I, III, V, and VI) and fibronectins, and is almost devoid of cells. The fibroblast layer is the thickest layer of the amnion and comprises fibroblasts and extracellular matrix components, such as collagens (e.g., collagen types I, III, and VI) and non-collagenous glycoproteins (e.g., laminins, fibronectins, and nidogens).

Intermediate layer, or spongy layer, is the interface between amnion and chorion. The intermediate layer comprises extracellular matrix components, such as collagens (e.g., collagen types I, III, and IV), proteoglycans, glycoproteins, and glycosaminoglycans (e.g. hyaluronic acid). Glycosaminoglycans, proteoglycans, and collagens lend additional firmness, elasticity, and strength to the intermediate layer and the layers attached to it. These proteins are also understood to play an important role in all stages of the wound healing cascade. In some embodiments, "intermediate layer" includes cells or extracellular matrix from an intermediate layer.

Chorion is several times thicker than amnion and is composed of three layers: a reticular layer, a basement membrane, and a trophoblast layer. The reticular layer is in contact with the intermediate layer and comprises extracellular components, such as collagens (e.g., collagen types I, III, IV, V, and VI) and proteoglycans. The basement membrane is between the reticular layer and trophoblast layer of the chorion. Components of the basement membrane of the chorion comprise collagens (e.g., collagen type IV), laminins, and fibronectins. The trophoblast layer comprises several layers of trophoblasts and is in contact with the maternal endometrium. As used herein, the term "trophoblast layer" includes cells, extracellular matrix, or blood vessels that may be present and that are derived from the capsular decidua, the portion of the maternal endometrium facing the uterine cavity.

II. Exemplary Embodiments of Products Made from Umbilical Cord

The umbilical cord connects the fetus to the placenta and allows the transfer of nutrients from the mother to the fetus. The umbilical cord is composed of a single umbilical vein and two umbilical arteries, which span between the placenta and the fetus. The vessels are surrounded by a thick layer of extracellular matrix called Wharton's Jelly, a gelatinous substance that insulates the vessels of the umbilical cord. The vessels and Wharton's Jelly are wrapped in umbilical cord amnion that is contiguous with the amnion of the placental membranes. Niknejad, H., et al., Properties of the amniotic membrane for potential use in tissue engineering. *European Cells and Materials* 15, 88-99 (2008). Sobolewski, K., et al., Collagen and Glycosaminoglycans of Wharton's Jelly. *Biology of the Neonate* 71, 11-21 (1997).

Umbilical cord, including the amnion and Wharton's jelly, is composed of many cells, extracellular matrix components, growth factors, and signaling molecules that are important in the wound healing cascade and tissue regeneration. For example, umbilical cord may contain cells, such as epithelial cells, stromal cells, mast cells, umbilical cord mesenchymal stem cells, and myofibroblast cells; extracellular matrix components, such as collagens (e.g. collagen types I, III, IV, V, VI, and VII), proteoglycans, such as decorins, laminin, elastins, fibrillin, and glycosaminoglycans, such as hyaluronic acid; growth factors and signaling molecules, such as epidermal growth factor, platelet derived growth factors, fibroblast growth factors, transforming growth factor beta and transforming growth factor alpha, metalloproteinases, tissue inhibitors of metalloproteinases (TIMPs), and insulin-like growth factors, etc.

Umbilical cord amnion is composed of a continuous layer of amnion epithelial cells that are present in the amnion membrane. Amniotic epithelial cells may include amniotic stem cells or have stem cell-like characteristics. For example, the cells of the epithelial layer of the amnion may be capable of differentiating into or producing, in the presence of a differentiation-inducing factor, at least one different cell lineage, such as osteogenic, adipogenic, chondrogenic, myogenic, neurogenic, epithelial, or other cell lineage. Amniotic stem cells or cells with stem cell-like characteristics may also be found in other layers of the amnion.

Amniotic epithelial cells may lack HLA-A, HLA-B (Class IA) and HA-DR (Class II) on their surfaces suggesting that these cells may be immunologically inert and have reduced risk of rejection or immune reaction upon transplantation.

Umbilical cord may be processed such that the epithelial layer of the amnion is maintained (intact), partially removed, or substantially removed. The epithelial layer may be removed, for example, by using a mechanical procedure or detergent-based procedure. In one embodiment, the epithelial cells are gently scraped away using a cell scraper with the aid of a microscope. In other embodiments, the epithelial layer is removed using an ionic detergent, a non-ionic detergent, or a zwitterionic detergent. As used herein, "partially removed" refers to a percentage of the epithelial layer having been removed in the range of 1% to 89% and "substantially removed" refers to a percentage of the epithelial layer having been removed in the range of 90% to 99%. In some embodiments, at least 10%, at least 20%, at least 30%, at least 40%, at least 50%, at least 60%, at least 70%, at least 80%, or at least 90% of the epithelial layer is removed.

Wharton's Jelly of the umbilical cord is a thick matrix containing suspended cells that may include stem cells or cells having stem cell-like characteristics. Wharton's Jelly cells may include myofibroblasts, mast cells, stromal cells, and mesenchymal stem cells. For example, cells of Wharton's Jelly may be capable of differentiating into or producing, in the presence of a differentiation-inducing factor, at least one different cell lineage, such as osteogenic, adipogenic, chondrogenic, myogenic, neurogenic, epithelial, or other cell lineage. The Wharton's Jelly further consists of extracellular matrix components, growth factors, and signaling molecules. For example, Wharton's Jelly may contain extracellular matrix components, such as collagens (e.g. collagen types I, III, IV, V, VI, and VII), proteoglycans, such as decorins, laminin, elastins, fibrillin, and glycosaminoglycans, such as hyaluronic acid; growth factors and signaling molecules, such as epidermal growth factor, platelet derived growth factors, fibroblast growth factors, transforming growth factor beta and transforming growth factor alpha, metalloproteinases, tissue inhibitors of metalloproteinases (TIMPs), and insulin-like growth factors, etc.

III. Exemplary Embodiments for Collecting and Evaluating Donor Placental Tissue

Placental tissue, including placental membranes and umbilical cord, may be collected from a human or other mammal, including but not limited to a primate, artiodactyl, perissodactyl, cow, bison, horse, pig, goat, or the like. Placental tissue may be recovered from a human during a full-term or near full-term Cesarean (C-section) birth. Potential donor mothers may be screened for risk factors to determine whether the placental tissue is safe and suitable for donation or processing. In one embodiment, a donor mother is tested for one or more viruses or bacteria using serological tests, which can include without limitation antibody, nucleic acid, or culture testing. The viral or bacterial screen may include screening for the human immunodeficiency virus type 1 or type 2 (HIV-1 and HIV-2), the hepatitis B virus (HBV), the hepatitis C virus (HCV), human T-lymphotropic virus type I or type II (HTLV-I and HTLV-II), CMV, the West Nile virus, or *Treponema pallidum* (a bacterium that causes syphilis). The placental tissue of a donor mother may be considered acceptable based on review of her health information or any screening test results.

A donor placental tissue may be recovered during an elective C-section procedure performed in a sterile operating room environment. A recovered placental tissue may be placed in a labeled, sterile container and submerged in a suitable storage medium. For example, a suitable storage medium includes a sodium chloride (NaCl) solution, such as a solution containing a w/v concentration of NaCl of 0.45%, 0.9%, 1.8%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, or at a w/v concentration of NaCl less than any of the concentrations listed above, greater than any of the concentrations listed above, of at least any of the concentrations listed above, or a range bounded by any two of the concentrations listed above, such as 0.45% to 36%, 0.45% to 5%, 5% to 10%, 10% to 20%, 20% to 30%, 20% to 25%, 25% to 30%, 30% to 36%, 0.45% to 15%, 15% to 33%, or 15% to 36%.

In addition, a suitable storage medium, such as a sodium chloride solution as described above, may also contains one or more of the following ingredients: phosphate, potassium, magnesium, calcium, dextrose, glucose, citrate, lactate, tris, or HEPES, etc. In some embodiments, a suitable storage medium comprises a buffer. Other suitable storage mediums include water (e.g., purified water, sterile water, or water for injection), Lactated Ringer's solution, Ringer's solution, phosphate-buffered saline (PBS), tris-buffered saline (TBS), Hank's balanced salt solution (HBSS), Dulbecco's phosphate-buffered saline (DPBS), Earle's balanced salt solution (EBSS), standard saline citrate (SSC), HEPES-buffered saline (HBS), Gey's balanced salt solution (GBSS), cell culture mediums (e.g., Delbecco's Modified Eagle Medium (DMEM), Minimum Essential Media (MEM), etc.), or other medium suitable for storing tissue.

The container may be shipped on wet ice to a processing laboratory for processing and evaluation. If the donor mother's health information and screening tests are satisfactory (i.e., indicate no risk or acceptable level of risk to human handling or use), the donor placental tissue may be processed for human medical applications.

After opening the shipment at the processing laboratory, personnel may verify that the sterile container or bag is still sealed and in coolant, and that the donor number on the accompanying paperwork matches the number on the sterile container. Processing of donor placental tissue for human medical applications may be conducted in a controlled, aseptic environment, such as in a hood or clean room.

IV. Exemplary Embodiments for Processing Placental Tissue

As used herein, "unseparated amnion/chorion" refers to the membrane portion of a placenta, irrespective of whether the membrane portion is attached to or detached from the placental disc and/or umbilical cord. In addition, unseparated amnion/chorion, as used herein, includes unseparated amnion/chorion processed by any step or any combination of steps selected from dissecting, cutting, washing, dehydrating, hydrating, and sterilizing.

In some embodiments, unseparated amnion/chorion is dissected from the placental disc and/or umbilical cord. An unseparated amnion/chorion may include an intermediate layer or may not include an intermediate layer, the inclusion or exclusion of which may depend on the characteristics of the donor placenta. In some embodiments, unseparated amnion/chorion comprises an epithelial layer of amnion (also referred to as intact). In some embodiments, the amnion epithelial layer of an unseparated amnion/chorion has been partially removed or substantially removed.

An unseparated amnion/chorion may be dissected away from the placental disc and/or umbilical cord or cut using any number of methods known to those of ordinary skill in the art, for example by using a scalpel, a pair of surgical scissors, a rotary blade, etc. In one embodiment, the placental tissue may be transferred to a surface suitable for dissection, such as a soft, nonporous mat, and the unseparated amnion/chorion dissected away from the rest of the placenta, e.g., using surgical scissors or a scalpel.

Amnion with or without intermediate layer or chorion with or without intermediate layer may be separated before, during, or after any step or combination of steps selected from dissecting, cutting, washing, and hydrating. For example, separation may be performed by any method understood by a person of ordinary skill in the art, including, but not limited to, gently separating amnion from chorion by hand. In some embodiments, a separated amnion comprises an intermediate layer. In some embodiments, separated chorion comprises an intermediate layer.

In some embodiments, an intermediate layer may be substantially intact on a separated amnion. In some embodiments, an intermediate layer may be substantially intact on a separated chorion. In some embodiments, a substantially intact intermediate layer is one that appears to the naked eye to cover a separated amnion or a separated chorion without visible holes. In some embodiments, a substantially intact intermediate layer may appear to the naked eye to cover most of a separated amnion or a separated chorion. In some embodiments, a substantially intact intermediate layer may appear to the naked eye to cover most of a separated amnion or a separated chorion, but that lacks intermediate layer at some or all of the periphery of the tissue. In some embodiments, a substantially intact intermediate layer may appear to the naked eye to cover at least 60%, at least 65%, at least 70%, at least 75%, at least 80%, at least 85%, at least 90%, or at least 95% of a separated amnion or a separated chorion.

In some embodiments, a placental tissue may comprise a substantial amount of intermediate layer. In some embodiments, a substantial amount of intermediate layer includes that a detectable amount of intermediate layer is visualized by microscopy of a histological section of the tissue. In some embodiments, a substantial amount of intermediate layer may be quantified by a mean thickness ranging from less than one micrometer to greater than 600 micrometers, as determined using the methods described herein. For example, a substantial amount of intermediate layer may be quantified by a mean thickness of 1 µm, 2 µm, 3 µm, 4 µm, 5 µm, 10 µm, 15 µm, 20 µm, 25 µm, 30 µm, 35 µm, 40 µm, 45 µm, 50 µm, 55 µm, 60 µm, 65 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 310 µm, 320 µm, 330 µm, 340 µm, 350 µm, 360 µm, 370 µm, 380 µm, 390 µm, 400 µm, 410 µm, 420 µm, 430 µm, 440 µm, 450 µm, 460 µm, 470 µm, 480 µm, 490 µm, 500 µm, 510 µm, 520 µm, 530 µm, 540 µm, 550 µm, 560 µm, 570 µm, 580 µm, 590 µm, or 600 or less than any value listed above, greater than any value listed above, at least any value listed above, or a range of values bounded by any two of the values listed above, such as 1 µm to 500 µm, 1 µm to 200 µm, 1 µm to 150 µm, 1 µm to 5 µm, 5 µm to 25 µm, 5 µm to 200 µm, 25 µm to 50 µm, 50 µm to 100 µm, 100 µm to 250 µm, 250 µm to 500 µm, 100 µm to 600 µm, 1 µm to 600 µm, 1 µm to 100 µm, 10 µm to 100 µm, 10 µm to 150 µm, or 50 µm to 500 µm. Furthermore, a composition may comprise a tissue or a sheet with an intermediate layer having a mean thickness of any value or range of values listed above.

In some embodiments, a placental tissue may comprise a substantial amount of Wharton's Jelly. In some embodiments, a substantial amount of Wharton's Jelly includes that a detectable amount of Wharton's Jelly is visualized by microscopy of a histological section of the tissue. In some embodiments, a substantial amount of Wharton's Jelly may be quantified by a mean thickness ranging from less than one micrometer to greater than 600 micrometers, as determined using the methods described herein. For example, a substantial amount of Wharton's Jelly may be quantified by a mean thickness of 1 µm, 2 µm, 3 µm, 4 µm, 5 µm, 10 µm, 15 µm, 20 µm, 25 µm, 30 µm, 35 µm, 40 µm, 45 µm, 50 µm, 55 µm, 60 µm, 65 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 310 µm, 320 µm, 330 µm, 340 µm, 350 µm, 360 µm, 370 µm, 380 µm, 390 µm, 400 µm, 410 µm, 420 µm, 430 µm, 440 µm, 450 µm, 460 µm, 470 µm, 480 µm, 490 µm, 500 µm, 510 µm, 520 µm, 530 µm, 540 µm, 550 µm, 560 µm, 570 µm, 580 µm, 590 µm, or 600 or less than any value listed above, greater than any value listed above, at least any value listed above, or a range of values bounded by any two of the values listed above, such as 1 µm to 500 µm, 1 µm to 5 µm, 5 µm to 25 µm, 25 µm to 50 µm, 50 µm to 100 µm, 100 µm to 250 µm, 250 µm to 500 µm, 100 µm to 600 µm, 1 µm to 600 µm, 1 µm to 100 µm, 10 µm to 100 µm, or 50 µm to 500 µm. Furthermore, a composition may comprise a tissue or a sheet with Wharton's Jelly having a mean thickness of any value or range of values listed above.

Thickness of a placental tissue, an intermediate layer, or Wharton's Jelly may be measured by microscopic analysis of histological sections. A portion of a placental tissue may be embedded, sectioned, mounted, and stained with hematoxylin and eosin (H & E). A digital image of each slide can be obtained. Approximate thickness of a placental tissue, intermediate layer, or Wharton's Jelly may be measured at one or several representative areas under magnification or using software. Mean thicknesses may be determined by calculating the average of the measured values.

As used herein, "umbilical cord" refers to the umbilical cord portion of placental tissue, irrespective of whether the umbilical cord is attached to or detached from the placental disc and membranes. In addition, umbilical cord, as used herein, includes umbilical cord processed by any step or any combination of steps selected from dissecting, cutting, washing, dehydrating, hydrating, and sterilizing.

In some embodiments, umbilical cord is dissected from the placental membranes and/or the placental disc. In some embodiments, umbilical cord comprises Wharton's Jelly and amnion. In some embodiments, umbilical cord comprises Wharton's Jelly. In some embodiments, umbilical cord comprises Wharton's Jelly and amnion, wherein the epithelial layer of the amnion has been partially removed or substantially removed.

Umbilical cord may be dissected away from the placental disc and/or membrane or cut using any number of methods known to those of ordinary skill in the art, for example by using a scalpel, a pair of surgical scissors, a rotary blade, etc. In one embodiment, the placental tissue may be transferred to a surface suitable for dissection, such as a soft, nonporous mat, and the umbilical cord dissected away from the rest of the placenta, e.g., using surgical scissors or a scalpel.

Umbilical cord may be dissected to completely, substantially, or partially remove the vessel walls of the umbilical cord vein and arteries. An umbilical cord may be dissected to remove the vessel walls using any number of methods known to those of ordinary skill in the art, for example by using a scalpel, a pair of surgical scissors, a pair of forceps, a rotary blade, etc.

A placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, may be cut into one or more sheets before, during, or after any step or any combination of steps selected from dissecting, washing, any dehydration step, any hydration step, or sterilizing. For example, a placental tissue sheet may be cut into 1 sheet, 2 sheets, 3 sheets, 4 sheets, 5 sheets, 6 sheets, 7 sheets, 8 sheets, 9 sheets, 10 sheets, 11 sheets, 12 sheets, 13 sheets, 14 sheets, 15 sheets, 16 sheets, 17 sheets, 18 sheets, 19 sheets, 20 sheets, or less than any number of sheets listed above, greater than any number of sheets listed above, at least any number of sheets listed above, or a range of sheets bounded by any two numbers listed above. In addition, in other embodiments, a placental tissue sheet may be cut into one or more additional sheets before, during, or after any step or any combination of steps selected from dissecting, washing, dehydrating, hydrating, and sterilizing. As used herein, "sheet" includes any three-dimensional conformation that may be formed from the sheet, including but not limited to, a cylindrical shape (e.g., sleeve), a cone shape, etc.

A placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, may be cut to any shape or size that the tissue may accommodate. For example, a placental tissue may be cut to or may have a regular or irregular shape. In some embodiments, a placental tissue may be cut to or may have the shape of a square, rectangle, oval, triangle, or circle, etc. In other embodiments, a placental tissue may be cut to have or may have one or more straight or curved edges.

A placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, may be cut to or may have any diameter that the tissue may accommodate, such as a diameter of 1 mm, 2 mm, 3 mm, 4 mm, 5 mm, 6 mm, 7 mm, 8 mm, 9 mm, 10 mm (or 1 cm), 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, or less than any value listed above, greater than any value listed above, at least any value listed above, or a range of values bounded by any two of the values listed above, such as 1 mm to 5 mm, 1 cm to 5 cm, 10 cm to 15 cm, 1 mm to 20 cm, 1 mm to 10 mm, 10 mm to 10 cm, 10 cm to 20 cm.

A placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, may be cut to or may have any length or width that the tissue may accommodate, such as a length or width of 1 mm, 2 mm, 3 mm, 4 mm, 5 mm, 6 mm, 7 mm, 8 mm, 9 mm, 10 mm (or 1 cm), 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, or less than any value listed above, greater than any value listed above, at least any value listed above, or a range of values bounded by any two of the values listed above, such as 1 mm to 5 mm, 1 cm to 5 cm, 10 cm to 15 cm, 1 mm to 20 cm, 1 mm to 10 mm, 10 mm to 10 cm, 10 cm to 20 cm.

In some embodiments, a dehydrated placental tissue has a marking, such as an embossment, a stain, a tint, a stamp, an opening, or a cut.

A placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, may be perforated before, during, or after any step or any combination of steps selected from dissecting, cutting, washing, sterilizing, and preserving (e.g., dehydrating).

As used herein, "perforate," refers to making a plurality of holes in a substrate.

For example, a placental tissue may be perforated using any of the methods described in WO 2017/049210, which is incorporated by reference in its entirety.

A placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, may comprise a plurality of perforations.

As used herein, a "plurality of perforations" refers to multiple holes having any shape or pattern.

In some embodiments, a plurality of perforations may have any depth ranging from less than a micron to greater than several millimeters. The depth of a hole may be determined by measuring the distance between one opening of the hole to the other opening of the hole. In some embodiments, the depth of a hole may be 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 25 µm, 30 µm, 40 µm, 50 µm, 60 µm, 70 µm, 80 µm, 90 µm, 100 µm (0.1 mm), 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 10 mm, or less than any value listed above, greater than any value listed above, at least any value listed above, or a range of values bounded by any two of the values listed above, such as 1 µm to 5 µm, 5 µm to 10 µm, 15 µm to 25 µm, 50 µm to 0.1 mm, 0.1 mm to 0.5 mm, 1 mm to 10 mm, 1 µm to 100 µm, 0.1 mm to 10 mm, or 1 µm to 10 mm.

In some embodiments, a plurality of perforations may have any opening area ranging from less than a square micron to greater than several square centimeters. In some embodiments, a hole may have an area of 1 µm², 2 µm², 3 µm², 4 µm², 5 µm², 6 µm², 7 µm², 8 µm², 9 µm², 10 µm², 11 µm², 12 µm², 13 µm², 14 µm², 15 µm², 16 µm², 17 µm², 18 µm², 19 µm², 20 µm², 25 µm², 30 µm², 40 µm², 50 µm², 60 µm², 70 µm², 80 µm², 90 µm², 100 µm² (0.1 mm²), 0.2 mm², 0.3 mm², 0.4 mm², 0.5 mm², 0.6 mm², 0.7 mm², 0.8 mm², 0.9 mm², 1 mm², 2 mm², 3 mm², 4 mm², 5 mm², 6 mm², 7 mm², 8 mm², 9 mm², 10 mm² (1 cm²), 2 cm², 3 cm², 4 cm², 5 cm² 6 cm², 7 cm², 8 cm², 9 cm², 10 cm², or less than any value listed above, greater than any value listed above, at least any value listed above, or a range of values bounded by any two of the values listed above, such as 1 µm² to 10 µm², 10 µm² to 100 µm², 100 µm² to 1 mm², 1 mm² to 10 mm², or 1 cm² to 10 cm², 1 µm² to 100 µm², 0.1 mm² to 10 mm², or 1 µm² to 10 cm².

In some embodiments, the distance between any two perforations may range from less than a micron to greater than several millimeters. The distance between any two adjacent holes may be determined by measuring the distance between the two closest points on the boundaries of the respective holes. In some embodiments, two holes may be separated by a distance of 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 25 µm, 30 µm, 40 µm, 50 µm, 60 µm, 70 µm, 80 µm, 90 µm, 100 µm (0.1 mm), 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 10 mm, or less than any value listed above, greater than any value listed above, at least any value listed above, or a range of values bounded by any two of the values listed above, such as 1 µm to 10 µm, 10 µm to 50 µm, 50 µm to 100 µm, 0.1 mm to 1 mm, 1 mm to 10 mm, 1 µm to 10 mm, 1 µm to 100 µm, or 0.1 mm to 10 mm.

A placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, may be pretreated and/or washed.

As used herein, "pretreat" is one or more steps intended to remove material (e.g., blood remnants or other debris) from the surface or loosen material from the interior of a placental tissue by any number of methods, including but not limited to picking, dabbing, rubbing, massaging with a fingertip, swab, or gauze, or flushing.

Pretreatment may be performed manually. In some embodiments, the pretreating is performed in the presence of a suitable washing medium. In some embodiments, placental tissue may be pretreated before, during, or after any step or any combination of steps selected from dissecting, separating, cutting, and washing. For example, in some embodiments, a placental tissue is pretreated before or after cutting.

As used herein, "wash" refers to trying to remove material (e.g., blood remnants or other debris) from the surface or interior of a placental tissue in the presence of a suitable washing medium by any number of methods, including but not limited to flushing, immersing, perfusing, soaking, or agitating in the presence or absence of pressure or vacuum.

For example, a placental tissue may be washed using any of the methods described in WO 2017/049210 and/or WO 2017/049215, which are incorporated by reference in their entirety.

In some embodiments, the agitating is performed using a rocker, shaker, stir plate, rotating mixer, or other equipment capable of agitating. In some embodiments, a placental tissue may be washed before, during, or after any step or any combination of steps selected from dissecting, separating, pretreating, deveining, and cutting.

In some embodiments, the material sought to be removed from the surface or interior of a placental tissue is blood remnants (e.g., blood clots, whole blood, intact blood cells, blood cell remnants, etc.) or other debris. In some embodiments, e.g., following pretreatment or washing, a placental tissue is substantially free of blood remnants.

As used herein, "substantially free" refers to a significantly reduced amount of an agent referenced. In some embodiments, the reduction in amount is greater than 50%. In some embodiments, the reduction in amount is greater than 60%, 70%, 80%, 90%, or 95%.

In some embodiments, a placental tissue has a hemoglobin content of less than a value, of greater than a value of, of at least a value, of a value, or ranging from any two values, wherein the value is selected from 13 ng/mg, 12 ng/mg, 11 ng/mg, 10 ng/mg, 9 ng/mg, 8 ng/mg, 7 ng/mg, 6 ng/mg, 5 ng/mg, 4 ng/mg, 3 ng/mg, 2 ng/mg, 1 ng/mg, 0.9 ng/mg, 0.8 ng/mg, 0.7 ng/mg, 0.6 ng/mg, 0.5 ng/mg, 0.4 ng/mg, 0.3 ng/mg, 0.2 ng/mg, 0.1 ng/mg, 0.09 ng/mg, 0.08 ng/mg, 0.07 ng/mg, 0.06 ng/mg, 0.05 ng/mg, 0.04 ng/mg, 0.03 ng/mg, 0.02 ng/mg, and 0.01 ng/mg.

In one embodiment, a suitable washing medium includes a sodium chloride solution, such as a solution containing a w/v concentration of NaCl of 0.45%, 0.9%, 1.8%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 34%, 35%, 36%, or less than any percentage listed above, greater than any percentage listed above, at least any percentage listed above, or a range of percentages bounded by any two of the percentages listed above, such as 0.45% to 5%, 5% to 10%, 10% to 20%, 20% to 30%, 20% to 25%, 25% to 30%, 30% to 36%, 0.45% to 15%, 15% to 33%, or 15% to 36%.

In addition, a suitable washing medium as described above may comprise one or more ingredients selected from phosphate, potassium, magnesium, calcium, dextrose, glucose, citrate, lactate, TRIS, and HEPES, etc.

Other suitable washing mediums include water (e.g., purified or sterile), Lactated Ringer's solution, Ringer's solution, phosphate-buffered saline (PBS), tris-buffered saline (TBS), Hank's balanced salt solution (HBSS), Dulbecco's phosphate-buffered saline (DPBS), Earle's balanced salt solution (EBSS), standard saline citrate (SSC), HEPES-buffered saline (HBS), Gey's balanced salt solution (GBSS), cell culture mediums (e.g., Delbecco's Modified Eagle Medium (DMEM), Minimum Essential Media (MEM), etc.), hydrogen peroxide solutions, sodium hypochlorite solutions, or other medium suitable for washing tissue.

A placental tissue may be washed in at least one suitable washing medium over one or more washing steps. For example, a placental tissue may be washed in at least one washing step, at least two washing steps, at least three washing steps, at least four washing steps, at least five washing steps, at least six washing steps, at least seven washing steps, at least eight washing steps, at least nine washing steps, at least ten washing steps, or ten or more washing steps.

In some embodiments, at least one washing step includes exchanging the at least one suitable washing medium at least once, once, at least twice, twice, at least thrice, thrice, at least four times, four times, at least five times, five times, at least six times, six times, at least seven times, seven times, at least eight times, eight times, at least nine times, nine times, at least ten times, ten times, or ten or more times. A suitable washing medium may be exchanged by transferring a placental tissue from old medium to fresh medium of the same or different type, or by removing some or all of the old medium and transferring fresh medium of the same or different type.

In other embodiments, at least one washing step includes comprises heating or cooling a placental tissue, or suitable washing medium.

For example, a placental tissue, or suitable washing medium may be placed in an environment having a temperature of 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., or less than any value listed above, greater than any value listed above, at least any value listed above, or a range of values bounded by any two of the values listed above.

A placental tissue or suitable washing medium may be placed in any of the environments listed above for any period of time ranging from minutes to hours. For example, the period of time may be 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 24 hours, 48 hours, 72 hours, or 96 hours, or less than any value listed above, greater than any value listed above, at least any value listed above, or a range of values bounded by any two of the values listed above, such as 5 minutes to 30 minutes, 30 minutes to 1 hour, 1 hour to 18 hours, 18 hours to 36 hours, 36 hours to 60 hours, 60 hours to 90 hours, 5 minutes to 24 hours, 24 hours to 48 hours, 72 hours to 96 hours, or 5 minutes to 96 hours.

The temperature of an environment in which a placental tissue or suitable washing medium is placed may change or may not change over time.

As used herein, "environment," includes, but is not limited to, a vessel (e.g., bag, container, dish, etc.), a medium (e.g., gas, fluid, etc.), a reservoir (e.g., a reservoir comprising a medium), a circuit, an oven, a freezer, a refrigerator, a freeze-dryer, a water bath, etc.

As used herein, a temperature of an environment "changes over time" when the environment is not at thermal equilibrium between any two points in time. As used herein, a temperature of an environment "does not change over time" when the environment is at thermal equilibrium between any two points in time. Thermal equilibrium includes a temperature differential of less than 1° C. In some embodiments, thermal equilibrium includes a temperature differential of less than 2° C. or 3° C.

A placental tissue described herein may be sterilized before, during, or after processing, including after final packaging. Sterilizing may be performed using one or more of any number of techniques, including but not limited to exposure to gamma radiation, E-beam radiation, ethylene oxide with a stabilizing gas (such as carbon dioxide or hydrochlorofluorocarbons (HCFC)), peracetic acid, hydrogen peroxide gas plasma, or ozone.

A placental tissue may be stored at refrigeration temperature for a limited time. For example, a placental tissue may be stored at a temperature of 1° C. to 12° C. or 1° C. to 5° C. for a time of 6 hours, 12 hours, 18 hours, 24 hours, 30 hours, 36 hours, 42 hours, 48 hours, 54 hours, 60 hours, 66 hours, 72 hours, 78 hours, 84 hours, 90 hours, or less than any time listed above, longer than any time listed above, at least any time listed above, or a range of times bounded by any two of the times listed above, such as 6 hours to 36 hours, 36 hours to 60 hours, 60 hours to 90 hours, or 6 hours to 90 hours.

V. Exemplary Embodiments of Dehydrating Placental Tissue

A placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, may be repeatedly dehydrated to produce a dehydrated placental tissue.

As used herein, "dehydrate" refers to removing any amount of moisture from a substrate using any one or a combination of techniques understood in the art. In some embodiments, some moisture is removed. In some embodiments, dehydrate includes removing some moisture, removing a substantial amount of moisture, or removing substantially all of the moisture.

In some embodiments, a dehydrated placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, appears dry. In some embodiments, a dehydrated placental tissue feels dry to the touch.

In some embodiments, moisture content of a dehydrated placental tissue may range from less than 0.5% to greater than 50%. Moisture content is reflected as a percentage of water weight per tissue weight. Moisture content is reported as a percentage water weight per tissue weight. Moisture content may be measured by Karl Fischer titration using methods understood in the art. In some embodiments, a dehydrated placental tissue has a moisture content of 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 20%, 25%, 30%, 35%, 40%, 45%, 50%, or less than any percentage listed above, greater than any percentage listed above, at least any percentage listed above, or a range of percentages bounded by any two of the percentages listed above, such as 0.5% to 50%, 0.5% to 0.9%, 1% to 2%, 2% to 3%, 3% to 5%, 5% to 7%, 7% to 10%, 10% to 12%, 12% to 15%, 0.5% to 5%, 5% to 10%, 10% to 15%, 2% to 4%, 4% to 6%, 6% to 8%, 8% to 10%, 1% to 15%, 1% to 10%, 10% to 20%, 10% to 30%, 20% to 30%, or 30% to 50%.

As used herein, "dehydration technique" refers to any one of a number of dehydration methods understood in the art.

In some embodiments, a dehydration technique comprises air drying. As used herein, "air drying" includes oven drying, drying with heated air, drying at ambient temperature, drying with cycled air (e.g., under vacuum), or drying with convection. In some embodiments, air drying includes using filtered air (e.g., by HEPA filtration). In some embodiments, a dehydration technique comprises chemical dehydration. In some embodiments, a dehydration technique comprises freeze drying.

As used herein, "a dehydration step" refers to a process of dehydrating a substrate, wherein the process has a beginning and an end and employs one or more dehydration technique(s) having one or more dehydration condition(s). Examples of dehydration conditions include, but are not limited to, temperature, time, pressure, environment, and/or medium, etc.

In some embodiments, a single dehydration step may employ two dehydration techniques. For example, a dehydration step may employ desiccation and oven drying. As another example, a dehydration step may employ chemical dehydration and air drying.

As used herein, "a dehydration environment" refers to at least one component involved in a dehydration technique or dehydration step. In some embodiments, a dehydration environment includes, but is not limited to, a vessel (e.g., bag, container, dish, etc.), a medium (e.g., gas, fluid, etc.), a reservoir (e.g., a reservoir comprising a medium), a circuit, an oven, a freezer, a refrigerator, a freeze-dryer, a water bath, etc.

In some embodiments, a placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, may be dehydrated by air drying, freeze drying, and/or chemical dehydration.

In some embodiments, a placental tissue may be repeatedly dehydrated using two dehydration steps, three dehydration steps, four dehydration steps, five dehydration steps, six dehydration steps, seven dehydration steps, eight dehydration steps, or any number of steps that is greater than eight.

In some embodiments, the final dehydration step comprises air drying. In some embodiments, a final dehydration step does not comprise chemical dehydration. In some embodiments, a final dehydration step does not comprise freeze drying. In some embodiments, the final dehydration step comprises oven dehydration or dehydration with ambient conditions.

In some embodiments, a dehydration technique used in one dehydration step may be the same as a dehydration technique used in any one of a number of other dehydration step(s), including the final dehydration step. In some embodiments, any two dehydration steps using the same technique may be separated by a hydration step. For example, a placental tissue may first be dehydrated in an oven, hydrated, and dehydrated in an oven again.

In other embodiments, a dehydration technique used for one dehydration step may be different from a dehydration technique used for any one of a number of other dehydration step(s), including the final dehydration step. In some embodiments, any two dehydration steps using a different technique are separated by a hydration step. For example, a placental tissue may be freeze dried, hydrated, and dehydrated in an oven.

In some embodiments, at least one dehydration technique or at least one dehydration step removes some moisture, a substantial amount of moisture, or all moisture. In some embodiments, at least one dehydration technique or at least one dehydrating step reduces the moisture content of the placental tissue by 99.9%, 99.8%, 99.7%, 99.6%, 99.5%, 99.4%, 99.3%, 99.2%, 99.1%, 99%, 98.5%, 98%, 97%, 96%, 95%, 94%, 93%, 92%, 93%, 92%, 91%, 90%, 85%, 80%, 75%, 70%, 65%, 60%, 55%, 50%, 45%, 40%, 35%, 30%, 25%, 20%, 15%, 10%, or 5%, or less than a value listed above, greater than a value listed above, at least a value listed above, or a range of values bounded by any two of the values listed above, such as 99.9% to 99%, 99.5% to 99%, 99% to 95%, 95% to 90%, 95% to 85%, 99% to 90%, 95% to 80%, 95% to 75%, 95% to 50%, 75% to 25%, 50% to 25%, 95% to 25%, or 50% to 10%.

In some embodiments, a method of preparing a dehydrated placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, comprises dehydrating the tissue in a first dehydration environment, hydrating the tissue in a hydration environment, and dehydrating the tissue in a second dehydration environment.

In some embodiments, a placental tissue may be dehydrated with air at or above ambient levels. In some embodiments, a placental tissue may be dehydrated using at least one dehydration technique comprising a dehydration environment having a temperature of or in at least one dehydration environment having a temperature of from 15° C. to 70° C., such as 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., or 70° C. or less than a value listed above, greater than a value listed above, at least a value listed above, or a range of values bounded by any two of the values listed above, such as 15° C. to 20° C., 32° C. to 34° C., 35° C. to 36° C., 32° C. to 43° C., 34° C. to 38° C., 61° C. to 69° C., 45° C. to 51° C., 56° C. to 7° C., 55° C. to 59° C., 41° C. to 47° C., 20° C. to 40° C., 30° C. to 50° C., or 40° C. to 60° C.

In some embodiments, a placental tissue may be dehydrated using at least one dehydration technique comprising a dehydration environment having a temperature of 15° C. or above or in at least one dehydration environment having a temperature of 15° C. or above and a vacuum pressure of from of from 0.0001 in Hg to 25 in Hg, such as 0.0001 inHg, 0.0005 in Hg, 0.001 in Hg, 0.005 in Hg, 0.01 in Hg, 0.05 in Hg, 0.1 in Hg, 0.2 in Hg, 0.3 in Hg, 0.4 in Hg, 0.5 in Hg, 0.6 in Hg, 0.7 in Hg, 0.8 in Hg, 0.9 in Hg, 1 in Hg, 2 in Hg, 3 in Hg, 4 in Hg, 5 in Hg, 6 in Hg, 7 in Hg, 8 in Hg, 9 in Hg, 10 in Hg, 11 in Hg, 12 in Hg, 13 in Hg, 14 in Hg, 15 in Hg, 16 in Hg, 17 in Hg, 18 in Hg, 19 in Hg, 20 in Hg, 21 in Hg, 22 in Hg, 23 in Hg, 24 in Hg, 25 in Hg, or less than a value listed above, greater than a value listed above, at least a value listed above, or a range of values bounded by any two values listed above, such as 0.0001 in Hg to 0.001 in Hg, 0.001 in Hg to 0.01 in Hg, 0.01 in Hg to 0.1 in Hg, 0.1 in Hg to 1 in Hg, 1 in Hg to 5 in Hg, 1 in Hg to 10 in Hg, 1 in Hg to 20 in Hg, 1 in Hg to 25 in Hg, 0.1 in Hg to 20 in Hg, or 0.01 in Hg to 1 in Hg.

In some embodiments, a placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, may be dehydrated by freeze-drying (also referred to as lyophilizing). See, e.g., U.S. Pat. No. 4,001,994 for a discussion of freeze-drying techniques. In some embodiments, a tissue may be frozen before lyophilizing. For example, a placental tissue may be quickly frozen by 100% ethanol and dry ice before lyophilizing or frozen less rapidly before lyophilizing. In some embodiments, a placental tissue may be stored for a period of time at a freezing temperature before lyophilizing, such as for 5 minutes, 15 minutes, 30 minutes, 1 hour, 2 hours, 3 hours, 6 hours, 12 hours, 18 hours, 24 hours, 30 hours, 36 hours, 42 hours, 48 hours, 54 hours, 60 hours, 66 hours, 72 hours, 78 hours, 84 hours, or 90 hours, less than any value listed above, greater than any value listed above, at least any value listed above, or a range of values bounded by any two of the values listed above, such as 5 minutes to 30 minutes, 30 minutes to 1 hour, 1 hour to 18 hours, 18 hours to 36 hours, 36 hours to 60 hours, 60 hours to 90 hours, 5 minutes to 24 hours, 24 hours to 90 hours, or 5 minutes to 90 hours.

In some embodiments, a placental tissue may be dehydrated using at least one dehydration technique (e.g., freeze drying) comprising a dehydration environment having a temperature of or in at least one dehydration environment having a temperature ranging from −100° C. to 0° C., such as −100° C., −99° C., −98° C., −97° C., −96° C., −95° C., −94° C., −93° C., −92° C., −91° C., −90° C., −89° C., −88° C., −87° C., −86° C., −85° C., −84° C., −83° C., −82° C., −81° C., −80° C., −79° C., −78° C., −77° C., −76° C., −75° C., −74° C., −73° C., −72° C., −71° C., −70° C., −69° C., −68° C., −67° C., −66° C., −65° C., −64° C., −63° C., −62° C., −61° C., −60° C., −59° C., −58° C., −57° C., −56° C., −55° C., −54° C., −53° C., −52° C., −51° C., −50° C., −49° C., −48° C., −47° C., −46° C., −45° C., −44° C., −43° C., −42° C., −41° C., −40° C., −39° C., −38° C., −37° C., −36° C., −35° C., −34° C., −33° C., −32° C., −31° C., −30° C., −29° C., −28° C., −27° C., −26° C., −25° C., −24° C., −23° C., −22° C., −21° C., −20° C., −19° C., −18° C., −17° C., −16° C., −15° C., −14° C., −13° C., −12° C., −11° C., −10° C., −9° C., −8° C., −7° C., −6° C., −5° C., −4° C., −3° C., −2° C., −1° C., or 0° C. or less than a value listed above, greater than a value listed above, at least a value listed above, or a range of values bounded by any two of the values listed above, such as −100° C. to −80° C., −80° C. to −60° C., −70° C. to −40° C., −60° C. to −30° C., −20° C. to 0° C., −50° C. to 0° C., −80° C. to −40° C., or −32° C. to −10° C.

In some embodiments, a placental tissue may be dehydrated using at least one dehydration technique (e.g., freeze drying) comprising a dehydration environment having a temperature of 0° C. or below or in at least one dehydration environment having a temperature of 0° C. or below and having a vacuum pressure of from 1 µbar to 65 mbar, such as 1 µbar, 10 µbar, 20 µbar, 30 µbar, 40 µbar, 50 µbar, 60 µbar, 70 µbar, 80 µbar, 90 µbar, 100 µbar, 200 µbar, 300 µbar, 400 µbar, 500 µbar, 600 µbar, 700 µbar, 800 µbar, 900 µbar, 1 mbar, 2 mbar, 3 mbar, 4 mbar, 5 mbar, 6 mbar, 7 mbar, 8 mbar, 9 mbar, 10 mbar, 11 mbar, 12 mbar, 13 mbar, 14 mbar, 15 mbar, 16 mbar, 17 mbar, 18 mbar, 19 mbar, 20 mbar, 21 mbar, 22 mbar, 23 mbar, 24 mbar, 25 mbar, 26 mbar, 27 mbar, 28 mbar, 29 mbar, 30 mbar, 31 mbar, 32 mbar, 33 mbar, 34 mbar, 35 mbar, 36 mbar, 37 mbar, 38 mbar, 39 mbar, 40 mbar, 41 mbar, 42 mbar, 43 mbar, 44 mbar, 45 mbar, 46 mbar, 47 mbar, 48 mbar, 49 mbar, 50 mbar, 51 mbar, 52 mbar, 53 mbar, 54 mbar, 55 mbar, 56 mbar, 57 mbar, 58 mbar, 59 mbar, 60 mbar, 61 mbar, 62 mbar, 63 mbar, or 64 mbar, or 65 mbar, or less than a value listed above, greater than a value listed above, at least a value listed above, or a range of values bounded by any two values listed above, such as from 1 µbar to 100 µbar, 1 µbar to 20 µbar, 1 µbar to 50 µbar, 30 µbar to 100 µbar, 50 µbar to 150 µbar, 1 µbar to 1 mbar, 500 µbar to 5 mbar, 1 mbar to 20 mbar, 5 mbar to 50 mbar, 1 mbar to 65 mbar, or 15 mbar to 50 mbar.

A placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, may also be dehydrated by chemical dehydration, for example by using a dehydration medium that decreases the water content of the product. A dehydration medium may comprise an alcohol, an organic solvent, a hydrophilic polymer (e.g., polyoxyethylene oxide), a polysaccharide (such as a cellulose derivative or dextrose, etc.), and/or a salt.

In some embodiments, a dehydration step may last for a period of time of 5 minutes, 15 minutes, 30 minutes, 1 hour, 2 hours, 3 hours, 4 hours, 6 hours, 7 hours, 8 hours, 12 hours, 15 hours, 18 hours, 20 hours, 24 hours, 30 hours, 36 hours, 42 hours, 48 hours, 54 hours, 60 hours, 66 hours, 72 hours, 78 hours, 84 hours, 90 hours, 96 hours, 102 hours, 108 hours, 114 hours, or 120 hours, or less than any value listed above, greater than any value listed above, at least any value listed above, or a range of values bounded by any two of the values listed above, such as 5 minutes to 1 hour, 1 hour to 4 hours, 1 hour to 8 hours, 4 to 15 hours, 15 hours to 18 hours, 4 hours to 36 hours, 8 hours to 24 hours, 15 hours to 20 hours, 18 to 24 hours, 24 to 36 hours, 4 to 72 hours, 24 to 120 hours, 66 to 120 hours, 96 to 120 hours, or 18 to 120 hours.

In some embodiments, the dehydration method described herein produces a translucent, dehydrated placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion.

As used herein, "translucency" refers to the extent to which visible light is permitted to pass through an object.

In some embodiments, translucency is evaluated by visual inspection. In some embodiments, translucency is quantified by measuring the percent light transmission through an object at one or multiple wavelengths. In some embodiments, percent light transmission is determined using a spectrophotometer by methods understood in the art.

As used herein, "light transmission" refers to the percent of light passing through an object at one or more wavelength(s).

As used herein, "translucent" refers to allowing a substantial amount of visible light to pass through an object.

In some embodiments, translucent includes allowing substantially all visible light to pass through an object. An example of a placental tissue or a portion thereof that allows substantially all visible light to pass through is a placental tissue or portion thereof that has been once dehydrated, hydrated, and then oven dehydrated a second time.

In some embodiments, a dehydrated placental tissue is translucent. In some embodiments, a translucent, dehydrated placental tissue allows substantially all visible light to pass through. In some embodiments, a translucent, dehydrated placental tissue appears translucent by visual inspection. For example, a dehydrated placental tissue may be held between a visible light source and a surface having marking(s) and it may be visually determined whether the marking(s) on the surface are visible through the tissue, such as visible to some degree.

In some embodiments, a portion of a dehydrated placental tissue is translucent. In some embodiments, a portion of a dehydrated placental tissue appears translucent by visual inspection. For example, a portion of a dehydrated placental tissue may be held between a visible light source and a surface having marking(s) and it may be visually determined whether the marking(s) on the surface are visible through the tissue, such as visible to some degree.

In some embodiments, substantially all of a dehydrated placental tissue is translucent. In some embodiments, substantially all of a dehydrated placental tissue appears translucent by visual inspection. For example, substantially all of a dehydrated placental tissue may be held between a visible light source and a surface having marking(s) and it may be visually determined whether the marking(s) on the surface are visible through the tissue, such as visible to some degree.

In some embodiments, at least 99%, at least 98%, at least 97%, at least 96%, at least 95%, at least 94%, at least 93%, at least 92%, at least 91%, at least 90%, at least 88%, at least 85%, at least 83%, and/or 80% of a dehydrated placental tissue is translucent. In some embodiments, at least 99%, at least 98%, at least 97%, at least 96%, at least 95%, at least 94%, at least 93%, at least 92%, at least 91%, at least 90%, at least 88%, at least 85%, at least 83%, and/or 80% of a dehydrated placental tissue appears translucent by visual inspection. For example, at least 99%, at least 98%, at least 97%, at least 96%, at least 95%, at least 94%, at least 93%, at least 92%, at least 91%, at least 90%, at least 88%, at least 85%, at least 83%, and/or 80% of a dehydrated placental tissue may be held between a visible light source and a surface having marking(s) and it may be visually determined whether the marking(s) on the surface are visible through the tissue, such as visible to some degree.

In some embodiments, a dehydrated placental tissue, a portion of a dehydrated placental tissue, substantially all of a dehydrated placental tissue, at least 99%, at least 98%, at least 97%, at least 96%, at least 95%, at least 94%, at least 93%, at least 92%, at least 91%, at least 90%, at least 88%, at least 85%, at least 83%, and/or 80% of a dehydrated placental tissue has a light transmission of from 5% to 90%, such as 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90%, or less than a value listed above, greater than a value listed above, at least a value listed above, or a range of values bounded by any two of the values listed above, such as 10% to 90%, 10% to 85%, 10% to 80%, 15% to 20%, 30% to 35%, 35% to 40%, 30% to 45%, 35% to 50%, 70% to 80%, 45% to 55%, 50% to 90%, 50% to 85%, 60% to 90%, 60% to 85%, 65% to 80%, 75% to 90%, 75% to 85%, 55% to 60%, or 40% to 50%, as determined by spectrophotometry at a wavelength of from 360 nm to 750 nm, such as at a wavelength of 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, and/or 750 nm, or less than a wavelength listed above, greater than a wavelength listed above, at least a wavelength listed above, or a range of wavelengths, such as from 370 nm to 400 nm, 370 nm to 750 nm, 390 nm to 700 nm, 500 nm to 750 nm, or 500 nm to 700 nm.

In some embodiments, a dehydrated placental tissue, a portion of the dehydrated placental tissue, substantially all of a dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of a placental tissue has a light transmission of greater than 25%, greater than 30%, greater than 40%, greater than 50%, greater than 60%, greater than 65%, greater than 70%, and/or greater than 75% as determined by spectrophotometry at a wavelength of 360 nm, 370 nm, 380 nm, and/or 390 nm.

In some embodiments, a dehydrated placental tissue, a portion of the dehydrated placental tissue, substantially all of a dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of a placental tissue has a light transmission of greater than 30%, greater than 40%, greater than 50%, greater than 60%, greater than 65%, greater than 70%, and/or greater than 75% as determined by spectrophotometry at a wavelength of 390 nm, 400 nm, 410 nm, and/or 420 nm.

In some embodiments, a dehydrated placental tissue, a portion of a dehydrated placental tissue, substantially all of the dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of a placental tissue has a light transmission of greater than 35%, greater than 30%, greater than 40%, greater than 50%, greater than 60%, greater than 65%, greater than 70%, and/or greater than 75% as determined by spectrophotometry at a wavelength of 430 nm, 440 nm, and/or 450 nm.

In some embodiments, a dehydrated placental tissue, a portion of a dehydrated placental tissue, substantially all of a dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of a placental tissue has a light transmission of greater than 40%, greater than 45%, greater than 50%, greater than 55%, greater than 60%, greater than 65%, greater than 68%, greater than 70%, greater than 75%, and/or greater than 80% as determined by spectrophotometry at a wavelength of 460 nm, 470 nm, and/or 480 nm.

In some embodiments, a dehydrated placental tissue, a portion of a dehydrated placental tissue, substantially all of a dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of a placental tissue has a light transmission of greater than 45%, greater than 50%, greater than 55%, greater than 60%, greater than 65%, greater than 70%, greater than 72%, greater than 75%, and/or greater than 80% as determined by spectrophotometry at a wavelength of 490 nm, 500 nm, 510 nm, 520 nm, and/or 530 nm.

In some embodiments, a dehydrated placental tissue, a portion of a dehydrated placental tissue, substantially all of a dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of a placental tissue has a light transmission of greater than 55%, greater than 60%, greater than 65%, greater than 70%, greater than 72%, greater than 73%, greater than 74%, greater than 75%, and/or greater than 80% as determined by spectrophotometry at a wavelength of 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, and/or 750 nm.

In some embodiments, a dehydrated placental tissue, a portion of a dehydrated placental tissue, substantially all of a dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of a placental tissue has a light transmission of greater than 60% as determined by spectrophotometry at a wavelength of 360 nm, 370 nm, 380 nm, 390 nm, 400 nm, and/or 410 nm.

In some embodiments, a dehydrated placental tissue, a portion of a dehydrated placental tissue, substantially all of a dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of a placental tissue has a light transmission of greater than 55%, greater than 56%, greater than 57%, greater than 58%, greater than 59%, and/or greater than 60% as determined by spectrophotometry at a wavelength of 360 nm, 370 nm, 380 nm, 390 nm, 400 nm, and/or 410 nm.

In some embodiments, a dehydrated placental tissue, a portion of a dehydrated placental tissue, substantially all of a dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of a placental tissue has a light transmission of from 55% to 80%, of from 56% to 80%, of from 57% to 80%, of from 58% to 80%, of from 59% to 80%, and/or of from 60% to 80% as determined by spectrophotometry at a wavelength of 360 nm, 370 nm, 380 nm, 390 nm, 400 nm, and/or 410 nm.

In some embodiments, a dehydrated placental tissue, a portion of a dehydrated placental tissue, substantially all of a dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of a placental tissue has a light transmission of greater than 65%, greater than 70%, or greater than 75%, and/or greater than 80% as determined by spectrophotometry at a wavelength ranging from 360 nm to 750 nm, and/or at a wavelength of 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, and/or 750 nm.

In some embodiments, a dehydrated placental tissue, a portion of a dehydrated placental tissue, substantially all of a dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of a placental tissue has a light transmission of greater than 80% as determined by spectrophotometry at a wavelength ranging from 580 nm to 750 nm, and/or at a wavelength of 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, and/or 750 nm.

In some embodiments, a dehydrated placental tissue, a portion of a dehydrated placental tissue, substantially all of a dehydrated placental tissue, or at least 99%, at least 98%, at least 97%, at least 96%, at least 95%, at least 94%, at least 93%, at least 92%, at least 91%, at least 90%, at least 88%, at least 85%, at least 83%, and/or 80% of a placental tissue has a light transmission of from 80% to 90%, of from 80% to 91% of from 80% to 92%, of from 80% to 93%, of from 80% to 94%, of from 80% to 95%, of from 80% to 96%, of from 80% to 97%, of from 80% to 98%, of from 80% to 99%, and/or of from 80% to 100% as determined by spectrophotometry at a wavelength ranging from 580 nm to 750 nm, and/or at a wavelength of 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, and/or 750 nm.

In some embodiments, light transmission is determined using a spectrophotometer (e.g., a X-RITE Color Eye spectrophotometer), such as a spectrophotometer having a 15 mm or 25 mm diameter aperture. In some embodiments, light transmission is determined using other standard transmission equipment.

In some embodiments, the light transmission is measured at at least one location, at least two different locations, at least three different locations, at least four different locations, at least five different locations, at least six different locations, or at more than six different locations of the tissue. In some embodiments, the light transmission is measured at at least one random location, at least two different random locations, at least three different random locations, at least four different random locations, at least five different random locations, at least six different random locations, or at more than six different random locations of the tissue. For example, one or more random locations may be selected without regard to the appearance of the tissue at that location(s). In some embodiments, the light transmission is measured at a series of locations spaced at intervals of 1, 2, 3, 5, 10, 15, 20, or 25 mm across a length or diameter of a placental tissue. In some embodiments, the light transmission is measured once, in duplicate, or in triplicate at any one or more location(s) of the tissue tested. In some embodiments, the light transmission is calculated as the average of multiple measurements taken at any one or more location(s) of the tissue tested, such as the average of all measurements at all tested locations of the tissue.

VI. Exemplary Embodiments of Hydrating Dehydrated Placental Tissue

In some embodiments, a method of preparing a dehydrated placental tissue, for example a placental tissue comprising intermediate layer, Wharton's Jelly, an unseparated amnion/chorion with or without intermediate layer, a separated amnion with or without intermediate layer, a separated chorion with or without intermediate layer, an umbilical cord (separated or unseparated) with or without Wharton's Jelly, and/or an umbilical cord amnion, comprises hydrating the tissue following any one of a number of dehydration step(s) and before the final dehydration step.

As used herein, "hydrate," refers to adding any amount of moisture to a substrate using any one or a combination of techniques understood in the art. In some embodiments, some moisture is added. In some embodiments, hydrate includes adding some moisture. In some embodiments, hydrate includes adding a substantial amount of moisture.

As used herein, "a hydration environment" refers to at least one component involved in adding moisture to a substrate. In some embodiments, a hydration environment includes, but is not limited to, a vessel (e.g., bag, container, dish, etc.), a medium (e.g., gas, fluid, etc.), a reservoir (e.g., a reservoir comprising a medium), a circuit, a humidifier, a water bath, etc.

In some embodiments, a placental tissue is hydrated between any two dehydration steps. For example, a placental tissue may first be dehydrated in an oven, hydrated, and dehydrated in an oven again. In some embodiments, a placental tissue may first be freeze-dried, hydrated, and dehydrated by air drying. In some embodiments, a placental tissue is air dried, hydrated, and then air dried again.

In some embodiments, a hydration step is performed after one dehydration step, after two dehydration steps, after three dehydration steps, after four dehydration steps, after five dehydration steps, after six dehydration steps, after seven dehydration steps, after eight dehydration steps, after nine dehydration steps, after ten dehydration steps, after all but the last dehydration step, or after a combination of any one dehydration step (except the final dehydration step).

In some embodiments, a placental tissue is hydrated between any two dehydration steps in a hydration environment for less than a period of time, greater than a period of time, at least a period of time, a period of time, or a range of any two periods of time, wherein the period of time is selected from 1 second, 30 seconds, 1 minute, 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 64 hours, and 72 hours.

In some embodiments, a placental tissue is hydrated in a hydration medium for less than a period of time of from 1 second to 72 hours, such as 1 second, 30 seconds, 1 minute, 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 64 hours, and 72 hours, or for a time period time less than any of the time periods listed above, greater than any of the time periods listed above, of at least any of the time periods listed above, or a range bounded by any two of the time periods listed above, such as 1 second to 5 minutes, 5 minutes to 20 minutes, 5 minutes to 1 hour, 1 hour to 2 hours, 30 minutes to 2 hours, 2 hours to 4 hours, 8 hours to 24 hours, 40 minutes to 12 hours, or 6 hours to 72 hours.

In some embodiments, a placental tissue is hydrated by immersing, perfusing, soaking, incubating, spraying, splashing, or flushing the tissue in or with a hydration medium. In some embodiments, a placental tissue is agitated while hydrating by shaking, massaging, inverting, or moving. In some embodiments, the agitating is performed using a rocker, a shaker, stir plate, rotating mixer, by hand, or other equipment capable of agitating.

In some embodiments, a placental tissue is hydrated between any two dehydration steps in a hydration environment comprising a hydration medium comprising water, saline, phosphate buffer, or cell culture media.

In some embodiments, a hydrating medium is selected from water, a sodium chloride solution, a sodium hypochlorite solution, a hydrogen peroxide solution, Lactated Ringer's solution, Ringer's solution, phosphate-buffered saline (PBS), tris-buffered saline (TBS), Hank's balanced salt solution (HBSS), Dulbecco's phosphate-buffered saline (DPBS), Earle's balanced salt solution (EBSS), standard saline citrate (SSC), HEPES-buffered saline (HBS), Gey's balanced salt solution (GBSS), and a cell culture medium. In some embodiments, the medium is a sodium chloride solution that comprises one or more ingredients selected from phosphate, potassium, magnesium, calcium, dextrose, glucose, citrate, lactate, tris, and HEPES. In some embodiments, the cell culture medium is Delbecco's Modified Eagle Medium (DMEM) or Minimum Essential Media (MEM).

In some embodiments, a placental tissue is placed in a hydrating environment or hydrating medium for any period of time ranging from minutes to hours. For example, the period of time may be 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 24 hours, 48 hours, 72 hours, or 96 hours, or less than any value listed above, greater than any value listed above, at least any value listed above, or a range of values bounded by any two of the values listed above, such as 5 minutes to 30 minutes, 30 minutes to 1 hour, 1 hour to 18 hours, 18 hours to 36 hours, 36 hours to 60 hours, 60 hours to 90 hours, 5 minutes to 24 hours, 24 hours to 48 hours, 72 hours to 96 hours, or 5 minutes to 96 hours.

In some embodiments, the temperature of the hydrating environment changes over time. In some embodiments, the temperature of hydrating environment does not change over time.

In some embodiments the hydration medium has a temperature of 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., or less than any value listed above, greater than any value listed above, at least any value listed above, or a range of values bounded by any two of the values listed above, such as refrigeration temperature, room temperature, or heated temperature.

VII. Exemplary Embodiments for Wound Healing

Placental tissues prepared as described herein and compositions comprising those placental tissues may be used in wound healing and applied to the eye, the skin, a nerve, a tendon, the dura, the abdomen, or an internal organ of a subject in need of treatment. For example, the placental tissues and compositions may be applied to a wound of the eye, such as a burn, a laceration, a corneal ulceration, a conjunctival lesion, or a surgical wound. The placental tissues and compositions may be applied to a wound of the skin, for example, a burn, a laceration, a diabetic ulcer, a venous ulcer, an arterial ulcer, a decubitus ulcer, or a surgical wound. Techniques for applying the compositions and products to a wound of the eye, the skin, a nerve, a tendon, the dura, the abdomen, or an internal organ are understood by those of ordinary skill in the art. In some embodiments, treating or covering a wound with the placental tissues described herein may prevent surgical adhesions and/or scarring.

EXAMPLES

Example 1. Repeated Oven Dehydration of Unseparated Amnion/Chorion A

Washed unseparated amnion/chorion samples were placed amnion side up on non-stick surface in a dish and dehydrated for a first time in an oven (Boekel Incubator, model #133000; Thelco Laboratory Precision Oven, Model #130) at various temperatures ranging from room temperature to 55° C., and for various times ranging from 4 to 36 hours. Table 1 summarizes the number and dryness of the samples tested under each dehydration condition.

TABLE 1

First Oven Dehydration Step of Unseparated Amnion/Chorion

| | | Time (hours) | | | | | | |
|---|---|---|---|---|---|---|---|---|
| | | 4 | 8 | 15 | 18 | 20 | 24 | 36 |
| Temperature | 25° C. | 1 ND | 1 ND | 1 D 2 ND | 2 ND | 2 ND | 2 D | 2 D |
| | 28° C. | 4 ND | 4 ND | 2 D 2 ND | 2 ND | 2 ND | 4 D 2 ND | 2 D |
| | 32-34° C. | 2 ND | 2 ND | 19 D 2 ND | 1 D 2 ND | 2 ND | 3 D 1 ND | 1 D |
| | 35-36° C. | NT | NT | 19 D | NT | NT | NT | NT |
| | 38° C. | 3 ND | 3 ND | 4 D | NT | NT | 3 D | NT |
| | 43° C. | 3 D 3 PD | NT | 8 D | NT | NT | 2 D | NT |
| | 55° C. | 1 D | NT | NT | NT | NT | NT | NT |

D indicates the dehydration condition was sufficient to dry to the touch the indicated number of samples tested;
ND indicates the dehydration condition was insufficient to dry to the touch the indicated number of samples tested;
NT means that no sample was tested at the dehydration condition indicated.

Twenty-four of the oven-dehydrated samples (dry to the touch) were hydrated in 100 mL of water for 30 minutes after the first dehydration cycle. The samples were again placed amnion side up on a non-stick surface in a dish and dehydrated for a second time in an oven at various temperatures ranging from 32° C. to 43° C. for either 4 hours or 15 hours (see Table 2).

TABLE 2

Two Oven Dehydration Steps of Unseparated Amnion/Chorion

| | | Dehydration Step 1 Time + Dehydration Step 2 Time (hrs) | | | |
|---|---|---|---|---|---|
| | | 15 hrs + 15 hrs | 15 hrs + 4 hrs | 4 hrs + 4 hrs | 24 hrs + 15 hrs |
| Temperature of Dehydration Step 2 | 32-34° C. | n = 2 | | | |
| | 35-36° C. | n = 5 | | | |
| | 38° C. | n = 2 | | | n = 3 |
| | 43° C. | n = 3 | n = 3 | n = 1 | n = 2 |

Figure 1B:
Figure 2A:
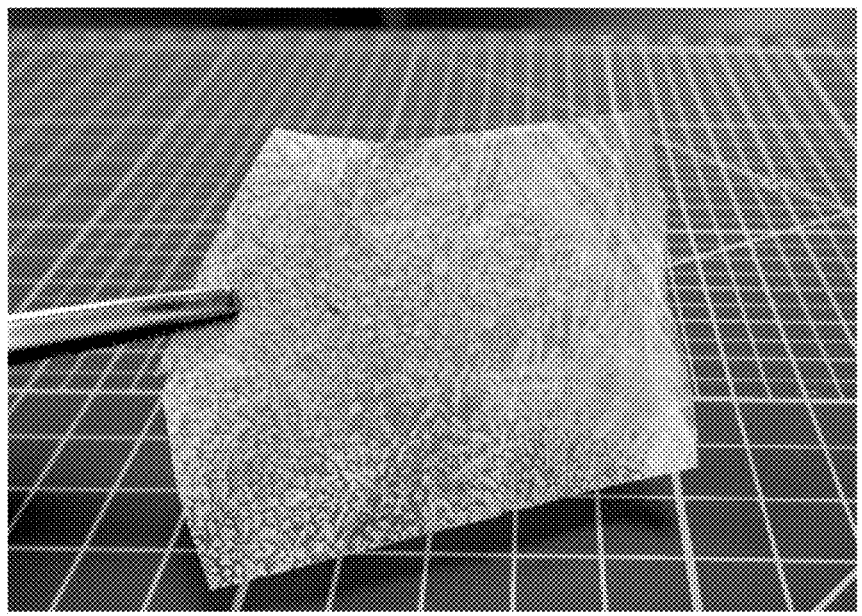
FIG. 2A and FIG. 2B show images of amnion with intermediate layer after a first oven-dehydration cycle (FIG. 2A) and after hydration followed by a second oven-dehydration cycle (FIG. 2B).

Following a first dehydration step, the tissue was brittle, was prone to cracking, and appeared white with branched structures (see, e.g., FIG. 2A). After hydration followed by a second dehydration step, the tissue was translucent, thinner and more pliable to the touch, and less prone to cracking (see, e.g., FIG. 1B) compared to after a first dehydration step.

Example 2. Repeated Dehydration of Unseparated Amnion/Chorion B

Washed unseparated amnion/chorion was placed amnion side up in a dish and frozen at −20° C. and then dehydrated for the first time in a freeze-drier (Labconco FreeZone 6 Freeze Dry System, Model #1103315) for 17 hours at 0.018 mbar of pressure and at −56° C., until dry to the touch. The freeze-dried sample was hydrated in 100 mL of water for 30 minutes. The sample was then placed amnion side up on a non-stick surface in a dish and dehydrated in an oven (Boekel Incubator, Model #133000) at 36° C. for 15 hours. The oven dehydrated sample was then hydrated for a second time in 100 mL of water for 30 minutes. The sample was again placed amnion side up on a non-stick surface in a dish and dehydrated in an oven (Thelco Laboratory Precision Oven, Model #130) at 50° C. for 3.5 hours.

Following the freeze-drying, the tissue was thick, white, and spongy. Following the second dehydration step, the tissue was considerably thinner to the touch, more translucent with some areas of white distortion. Following the third and final dehydration step, the tissue was thin, translucent, and papery.

Example 3. Repeated Dehydration of Unseparated Amnion/Chorion C

A washed unseparated amnion/chorion was placed amnion side up in a non-stick surface in a dish and dehydrated in a vacuum oven at 35° C. while pulling a continuous vacuum at a pressure of 10 in Hg (339 mbar) for 15-25 hours, until dry to the touch. The dehydrated sample was hydrated in 100 mL of water for 1 hour. The hydrated sample was again placed amnion side up on a non-stick surface in a dish and dehydrated in a vacuum oven at 35° C. while pulling a continuous vacuum at a pressure of 30 in Hg (1016 mbar) for 2 hours.

Following the first vacuum oven dehydration step, the tissue was brittle, was prone to cracking, and appeared to have white branched structures. Following the second vacuum oven dehydration step, the tissue was translucent, pliable, and less prone to cracking.

Example 4. Repeated Dehydration of Unseparated Amnion/Chorion D

A washed unseparated amnion/chorion was dehydrated by submerging in a 50% ethanol solution for 17 hours. Following chemical dehydration, the tissue was placed amnion side up on a non-stick surface in a dish and dried in an oven (Boekel Incubator, Model #133000) at 40° C. for 7.5 hours, until dry to the touch.

Following the first dehydration step (chemical dehydration), the tissue was thick, tough, wet, and opaque. After the second dehydration step (oven dehydration), the tissue was thinner, pliable, and translucent.

Example 5. Repeated Dehydration of Amnion/Intermediate Layer

Samples of washed amnion with intermediate layer were placed amnion side up on a non-stick surface in a dish and dehydrated for the first time in an oven (Boekel Incubator, Model #133000) at 39° for 19 hours, until dry to the touch. The oven-dehydrated samples were hydrated in 100 mL of water for 30 minutes. The samples were again placed amnion side up on a non-stick surface in a dish and dehydrated for a second time at various temperatures ranging from 33° C. to 55° C. using an incubator (Boekel Incubator, model #133000) or oven (Thelco Laboratory Precision Oven, Model #130) for time periods ranging from 1 hour to 5 hours.

Figure 2B:
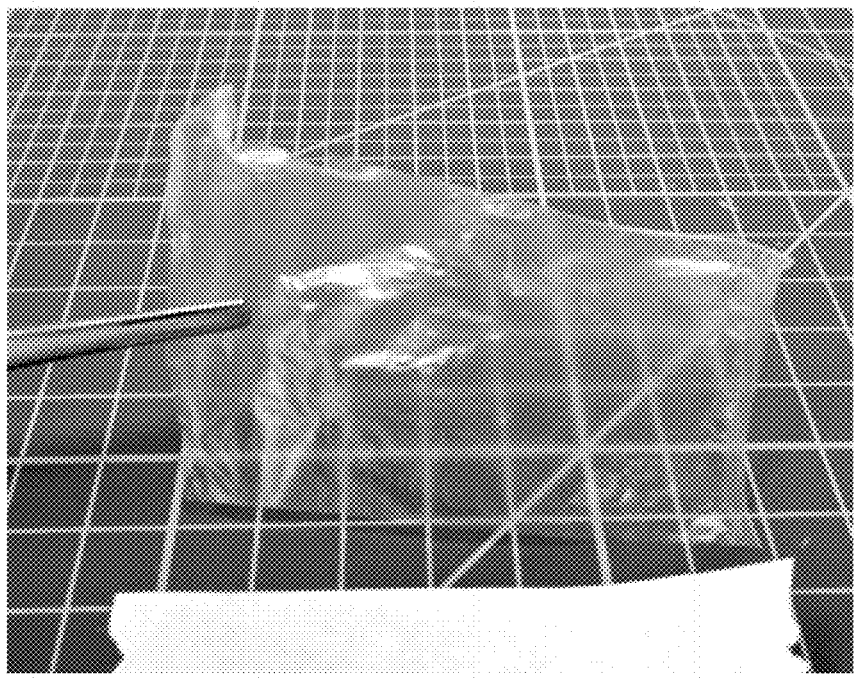

Following the first dehydration step, the tissue was brittle, prone to cracking, and appeared white with branched structures (see, e.g., FIG. 2A). After hydration followed by a second dehydration step, the tissue was translucent, thinner, pliable, and less prone to cracking (see, e.g., FIG. 2B).

Example 6. Repeated Oven Dehydration of Umbilical Cord

A dissected and washed umbilical cord sample was placed amnion side up on a non-stick surface in a dish and dehydrated for the first time in an oven (Thelco Laboratory Precision Oven, Model #130) at 60° for 4 hours, until dry to the touch. The oven-dehydrated sample was hydrated in 100 mL of water for 30 minutes. The samples were again placed amnion side up on a non-stick surface in a dish and baked for a second time in an oven (Thelco Laboratory Precision Oven, Model #130) at 55° C. for 2 hours.

Figure 3A:
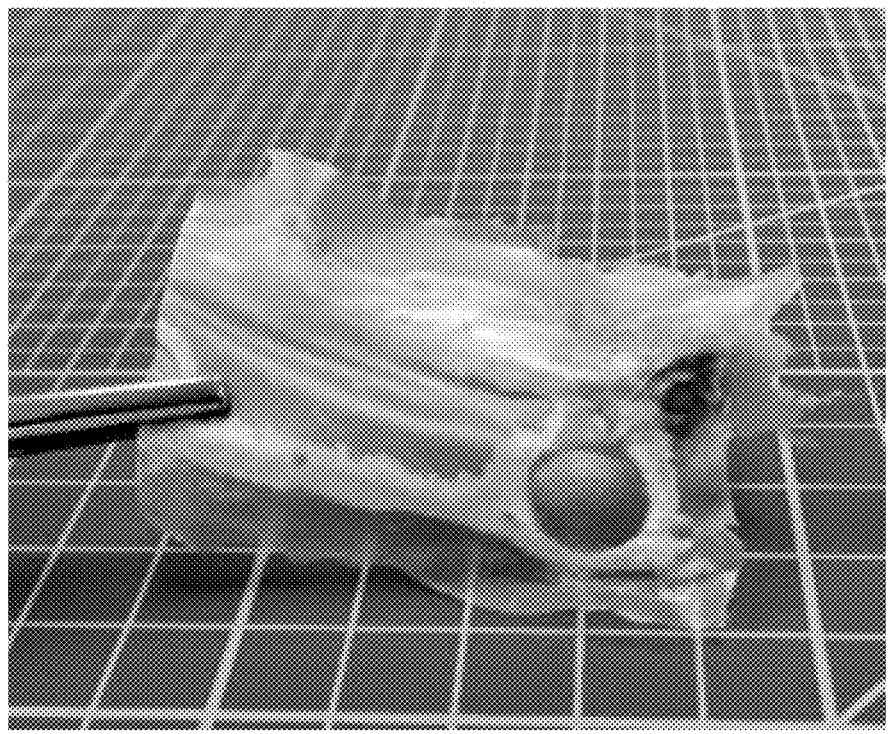
FIG. 3A and FIG. 3B show images of umbilical cord after a first oven-dehydration cycle (FIG. 3A) and after hydration followed by a second oven-dehydration cycle (FIG. 3B).
Figure 3B:

Following a first dehydration step, the tissue was brittle, unpliable, and appeared white with heavily clouded areas (see e.g., FIG. 3A). After hydration followed by a second dehydration step, the tissue was translucent, thinner, pliable, and less prone to cracking (see e.g., FIG. 3B).

Example 7. Histology of Oven Dehydration of Placental Membrane

Figure 4A:
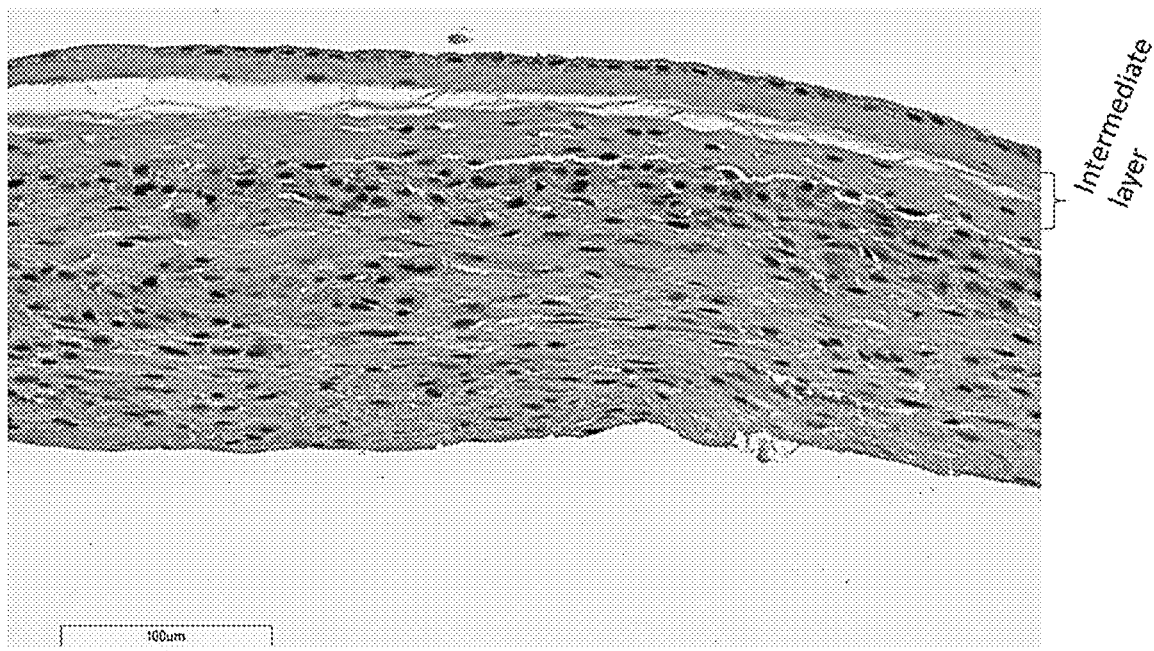
FIG. 4A and FIG. 4B show images of H&E staining of unseparated amnion/chorion after one oven dehydration cycle (FIG. 4A) and after hydration followed by a second oven dehydration cycle (FIG. 4B).
Figure 4B:
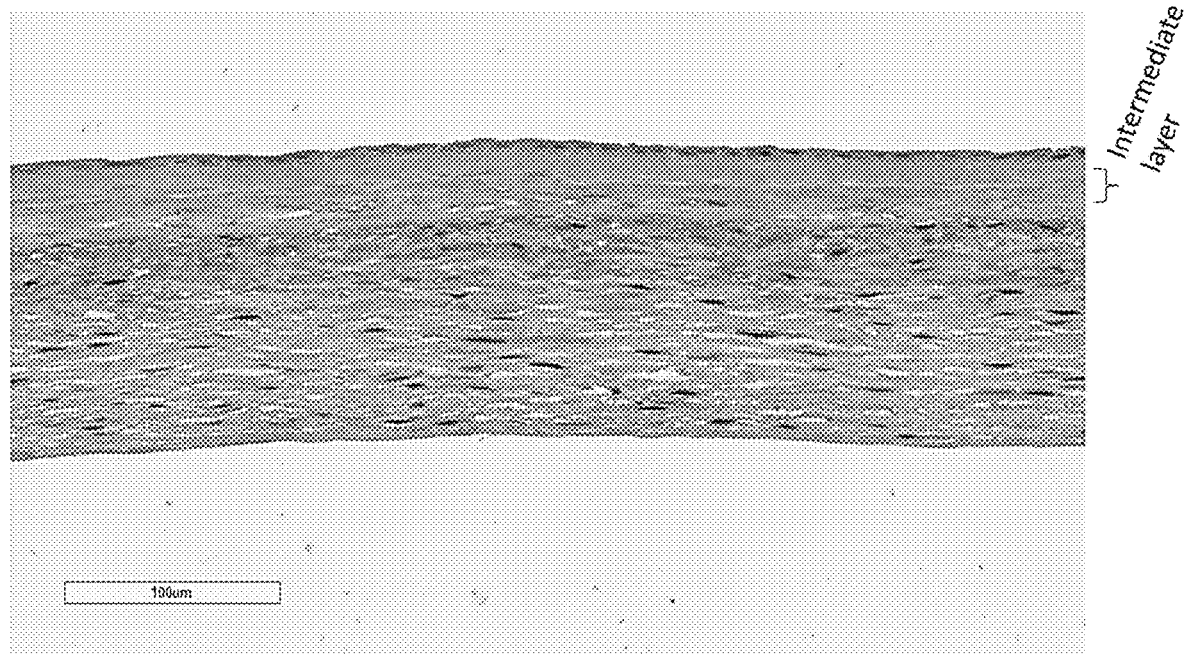

Histology (H&E staining) images of an unseparated amnion/chorion sample after one oven dehydration step (FIG. 4A) and after hydration followed by a second oven dehydration step (FIG. 4B) were compared. The intermediate layer appeared more compact after the second dehydration cycle.

Example 8. Light Transmission of Oven Dehydrated and Lyophilized Placental Membranes Translucency of (1) lyophilized, unseparated amnion/chorion samples (n=3; Samples 1-3); (2) single oven-dehydrated, unseparated amnion/chorion samples (n=6; Samples 4-9); and (3) double oven-dehydrated, unseparated amnion/chorion samples (with hydration between oven-dehydration cycles; n=3; Samples 10-12) was compared by visual inspection (FIG. 5A, FIG. 6A, FIG. 7A, and FIG. 8A) and by percent light transmission (FIG. 5B, FIG. 6B, FIG. 7B, and FIG. 8B). Percent light transmission at three different random locations of each sample was measured at wavelengths ranging from 360 nm to 750 nm in 10 nm increments using a spectrophotometer (X-RITE Color Eye 7000A) with a 25 mm diameter aperture. The average percent light transmission was plotted with respect to wavelength.

Figure 5A:
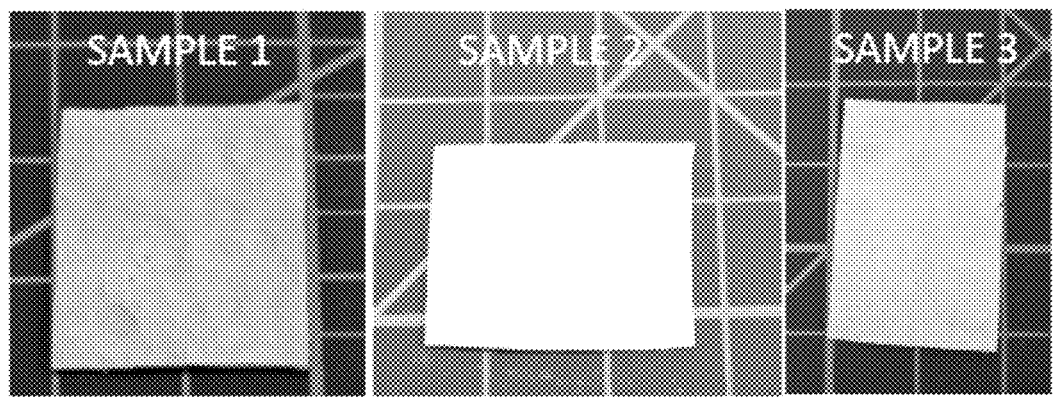
FIG. 5A shows images of three unseparated amnion/chorion samples (Samples 1-3) after lyophilization.
Figure 5B:
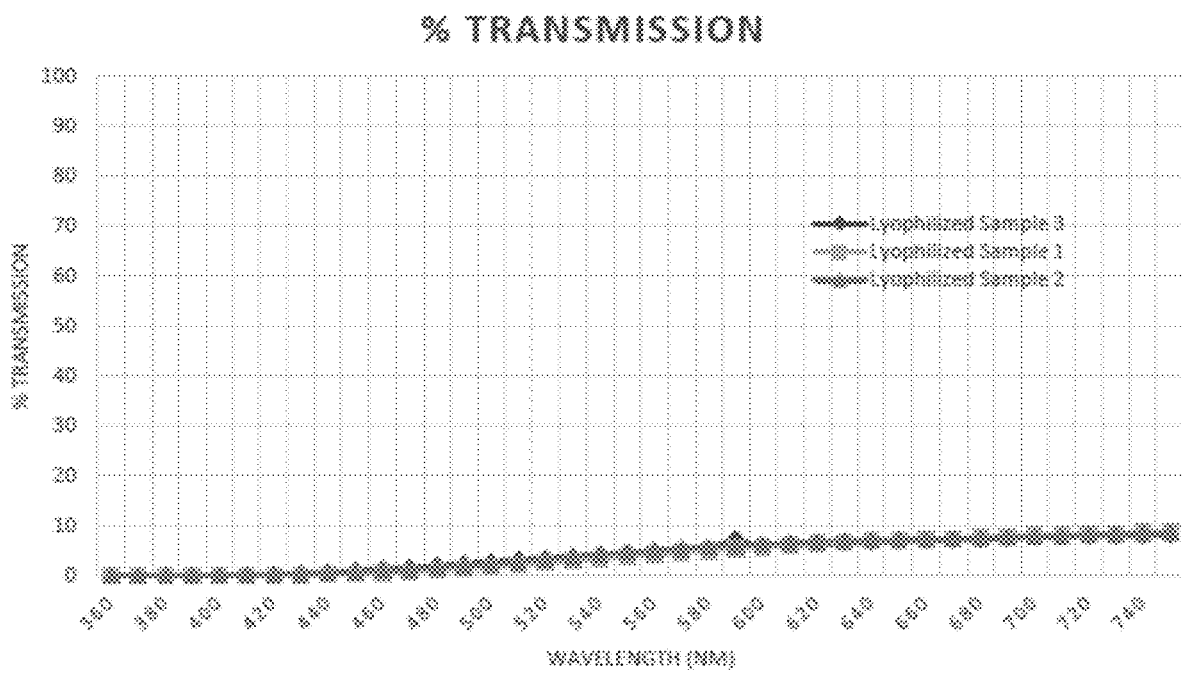
FIG. 5B shows a graph of percent light transmission of each sample measured at wavelengths ranging from 360 nm to 750 nm.
Figure 6A:
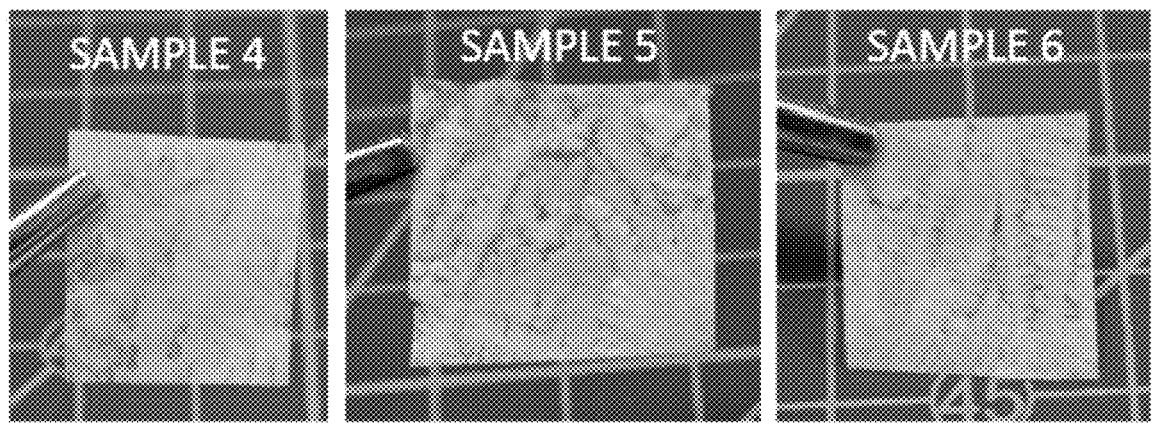
FIG. 6A shows images of three unseparated amnion/chorion samples (Samples 4-6) after oven dehydration.
Figure 6B:
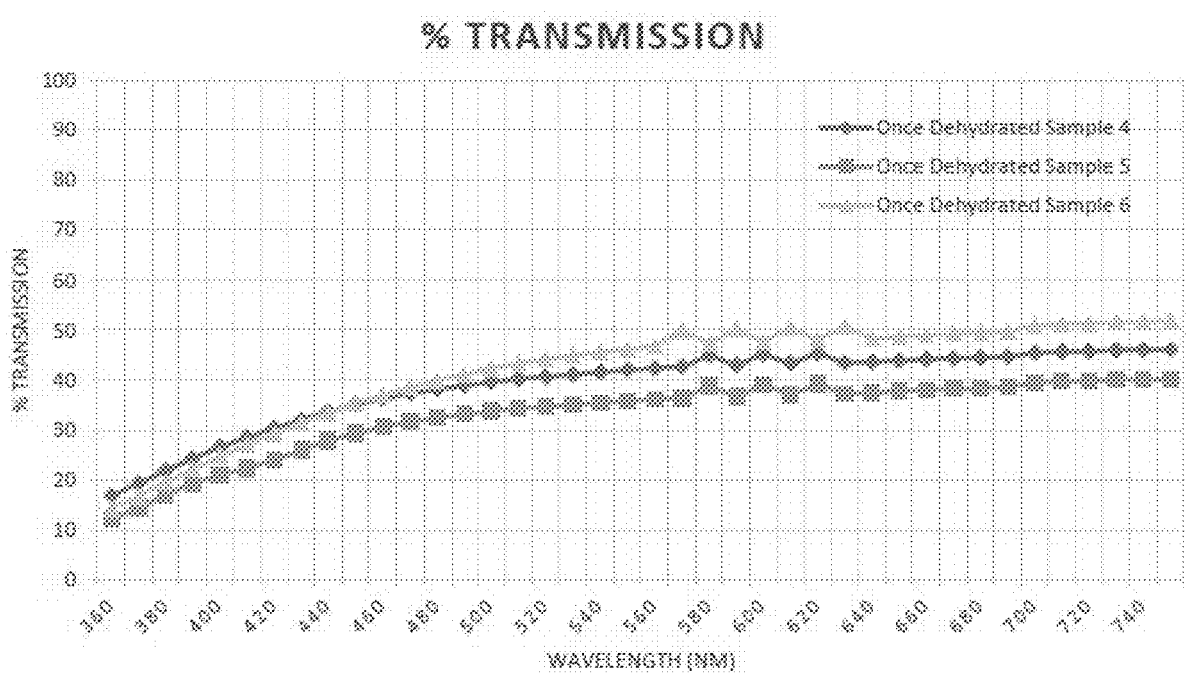
FIG. 6B shows a graph of percent light transmission of each sample measured at wavelengths ranging from 360 nm to 750 nm.
Figure 7A:
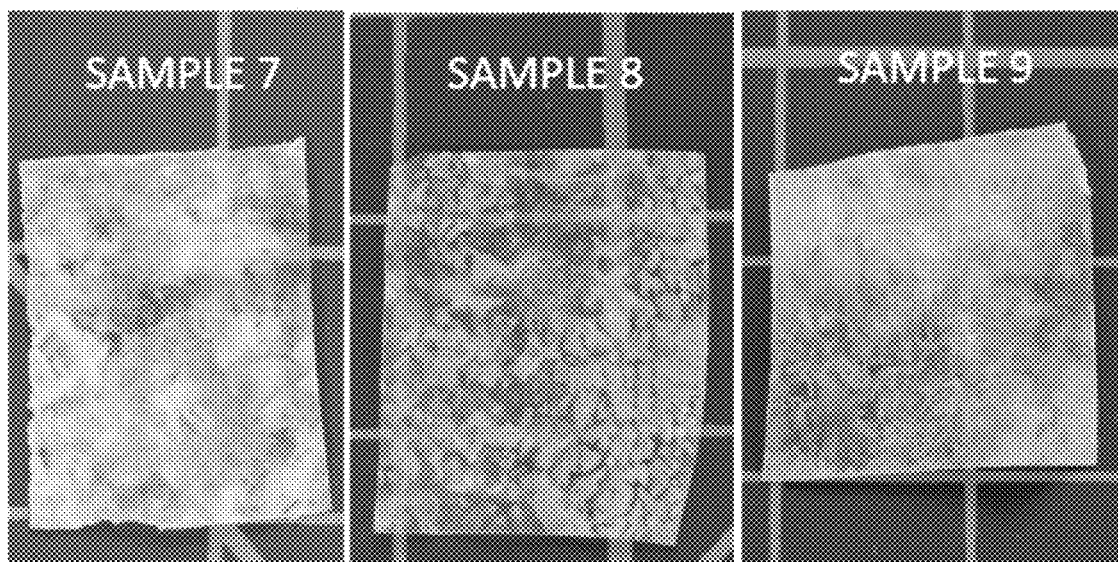
FIG. 7A shows images of three unseparated amnion/chorion samples (Samples 7-9) after oven dehydration.
Figure 7B:
FIG. 7B shows a graph of percent light transmission of each sample measured at wavelengths ranging from 360 nm to 750 nm.
Figure 8A:
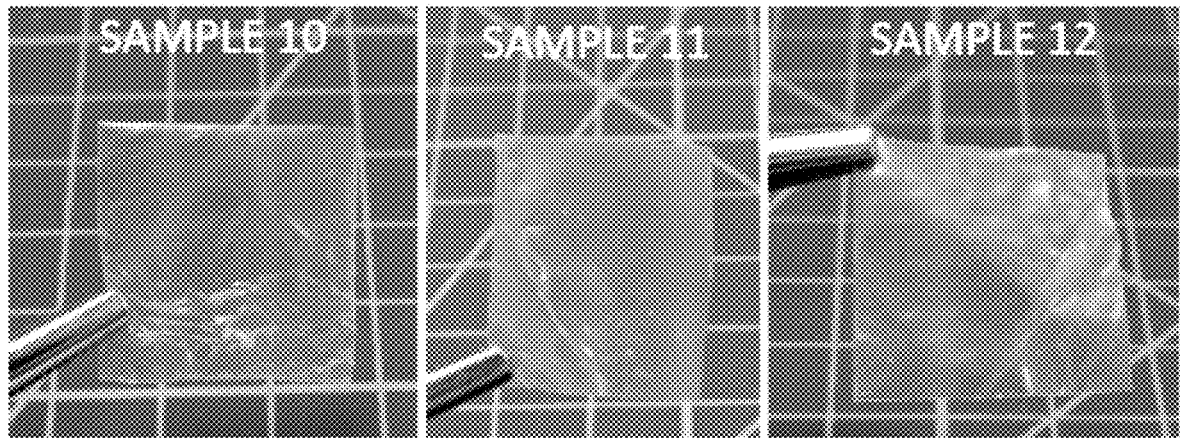
FIG. 8A shows images of three unseparated amnion/chorion samples (Samples 10-12) after a first oven-dehydration cycle, hydration, and a second oven-dehydration cycle.
Figure 8B:
FIG. 8B shows a graph of percent light transmission of each sample measured at wavelengths ranging from 360 nm to 750 nm.

The average percent light transmission was compared among images of samples tested. The amount of translucency detectable to the naked eye corresponded with the percent light transmission measured. The lyophilized samples, which were visibly opaque (FIG. 5A), had low light transmission values (e.g., less than 10% from 360 nm to 750 nm) (FIG. 5B). The double oven-dehydrated samples, which were visibly translucent (FIG. 8A), consistently had high light transmission values (e.g., greater than 80% between 580 nm and 750 nm) (FIG. 8B). The single oven-dehydrated samples, which appeared with white, heavily clouded areas and branched structures (FIG. 6A and FIG. 7A), had variable light transmission values falling between the lyophilized samples and the double oven-dehydrated samples (FIG. 6B and FIG. 7B).

What is claimed is:

1. A dehydrated placental tissue comprising Wharton's Jelly, wherein the dehydrated placental tissue is translucent.

2. The dehydrated placental tissue of claim 1, wherein the dehydrated placental tissue, a portion of the dehydrated placental tissue, substantially all of the dehydrated placental tissue, or at least 80% of the placental tissue:
    a) allows substantially all visible light to pass through;
    b) appears translucent by visual inspection; and/or
    c) appears translucent by visual inspection, as determined by holding the dehydrated placental tissue between a visible light source and a surface having marking(s) and visually detecting whether the marking(s) on the surface are visible through the tissue.

3. The dehydrated placental tissue of claim 1, wherein the dehydrated placental tissue, a portion of the dehydrated placental tissue, substantially all of the dehydrated placental tissue, or at least 80% of the placental tissue has a light transmission of:
    a) greater than 60% as determined by spectrophotometry at a wavelength of 460 nm, 470 nm, 480 nm, 490 nm, 500 nm, 510 nm, 520 nm, 530 nm, 540 nm, 550 nm, 560 nm, 570 nm, and/or 580 nm; and/or
    b) greater than 70% as determined by spectrophotometry at a wavelength of 470 nm, 480 nm, 490 nm, 500 nm, 510 nm, 520 nm, 530 nm, 540 nm, 550 nm, 560 nm, 570 nm, 580 nm, 590 nm, 600 nm, and/or 610 nm; and/or
    c) greater than 80% as determined by spectrophotometry at a wavelength ranging from 580 nm to 750 nm, and/or at a wavelength of 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, and/or 750 nm.

4. The dehydrated placental tissue of claim 1, wherein the dehydrated placental tissue is from a human donor.

5. The dehydrated placental tissue of claim 1, wherein the dehydrated placental tissue comprises unseparated umbilical cord, separated umbilical cord, and/or umbilical cord amnion.

6. The dehydrated placental tissue of claim 5, wherein the dehydrated placental tissue has a hemoglobin content of less than 13 ng/mg of dry mass of the tissue.

7. The dehydrated placental tissue of claim 5, wherein the dehydrated placental tissue has a hemoglobin content of less than 10 ng/mg of dry mass of the tissue.

8. The dehydrated placental tissue of claim 5, wherein the dehydrated placental tissue has a hemoglobin content of less than 5 ng/mg of dry mass of the tissue.

9. The dehydrated placental tissue of claim 5, wherein the dehydrated placental tissue appears dry, feels dry to the touch, and/or has a moisture content of from 0.5% to 50%.

10. The dehydrated placental tissue of claim 5, wherein the dehydrated placental tissue has a moisture content of from 0.5% to 50%.

11. The dehydrated placental tissue of claim 1, wherein the dehydrated placental tissue comprises a substantial amount of Wharton's Jelly.

12. The dehydrated placental tissue of claim 1, wherein the dehydrated placental tissue is substantially free of blood remnants and/or has a hemoglobin content of less than 13 ng/mg of dry mass of the tissue.

13. The dehydrated placental tissue of claim 1, wherein the dehydrated placental tissue appears dry, feels dry to the touch, and/or has a moisture content of from 0.5% to 50%.

14. The dehydrated placental tissue of claim 1, wherein the dehydrated placental tissue is sterile.

15. The dehydrated placental tissue of claim 1, wherein the dehydrated placental tissue is perforated.

16. A composition comprising the dehydrated placental tissue of claim 1.

17. The dehydrated placental tissue of claim 1, wherein the dehydrated placental tissue has a hemoglobin content of less than 10 ng/mg of dry mass of the tissue.

18. The dehydrated placental tissue of claim 1, wherein the dehydrated placental tissue has a hemoglobin content of less than 5 ng/mg of dry mass of the tissue.

19. The dehydrated placental tissue of claim 1, wherein at least 80% of the placental tissue appears translucent by visual inspection, as determined by holding the dehydrated placental tissue between a visible light source and a surface having marking(s) and visually detecting whether the marking(s) on the surface are visible through the tissue.

20. The dehydrated placental tissue of claim 1, wherein at least 80% of the placental tissue has a light transmission of:
   a) greater than 60% as determined by spectrophotometry at a wavelength of 460 nm, 470 nm, 480 nm, 490 nm, 500 nm, 510 nm, 520 nm, 530 nm, 540 nm, 550 nm, 560 nm, 570 nm, and/or 580 nm; and/or
   b) greater than 70% as determined by spectrophotometry at a wavelength of 470 nm, 480 nm, 490 nm, 500 nm, 510 nm, 520 nm, 530 nm, 540 nm, 550 nm, 560 nm, 570 nm, 580 nm, 590 nm, 600 nm, and/or 610 nm; and/or
   c) greater than 80% as determined by spectrophotometry at a wavelength ranging from 580 nm to 750 nm, and/or at a wavelength of 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, and/or 750 nm.

21. The dehydrated placental tissue of claim 1, wherein the dehydrated placental tissue has a moisture content of from 0.5% to 50%.

22. A method of treating or covering a wound of a subject comprising applying the dehydrated placental tissue of claim 1 to the wound of the subject.

23. The method of claim 22, wherein the wound is a wound of the eye, a wound of the skin, a wound of a nerve, a wound of a tendon, a wound of the dura, a periodontal wound, a wound of the abdomen, or a wound of an internal organ.

24. The method of claim 23, wherein the wound is a burn, a laceration, a corneal ulceration, a conjunctival lesion, a surgical wound, a diabetic ulcer, a venous ulcer, an arterial ulcer, or a decubitus ulcer.

* * * * *